United States Patent
Lee et al.

(10) Patent No.: US 11,266,603 B2
(45) Date of Patent: Mar. 8, 2022

(54) SYNTHETIC POLYPEPTIDES AND USES THEREOF

(71) Applicant: Academia Sinica, Taipei (TW)

(72) Inventors: Hsien-Ming Lee, Taipei (TW); Hua-De Gao, Taipei (TW); Jia-Lin Hong, Taipei (TW); Chih-Yu Kuo, Taipei (TW); Cheng-Bang Jian, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 16/455,800

(22) Filed: Jun. 28, 2019

(65) Prior Publication Data

US 2020/0000722 A1 Jan. 2, 2020

Related U.S. Application Data

(60) Provisional application No. 62/691,145, filed on Jun. 28, 2018.

(51) Int. Cl.
| | |
|---|---|
| *A61K 9/127* | (2006.01) |
| *C07K 14/00* | (2006.01) |
| *A61K 41/00* | (2020.01) |
| *A61K 49/00* | (2006.01) |
| *C07K 7/08* | (2006.01) |
| *A61K 31/704* | (2006.01) |

(52) U.S. Cl.
CPC .......... *A61K 9/1271* (2013.01); *A61K 31/704* (2013.01); *A61K 41/0042* (2013.01); *A61K 49/0032* (2013.01); *C07K 7/08* (2013.01); *C07K 14/001* (2013.01)

(58) Field of Classification Search
CPC ........ A61K 38/00; A61K 45/06; A61K 39/00; A61K 9/1271; A61K 47/6911; A61K 9/127; A61K 47/64; A61K 38/1729; A61K 47/6913; A61K 47/645; A61K 47/42; A61K 51/0497; A61K 51/1234; A61K 49/0466; A61K 49/1812; A61K 51/088; A61K 49/227; A61K 51/08; A61K 8/14; A61P 31/04; B82Y 5/00; A61L 2300/404
See application file for complete search history.

(56) References Cited

U.S. PATENT DOCUMENTS

| | | | | |
|---|---|---|---|---|
| 2007/0041904 | A1* | 2/2007 | Jiang | ........... A61P 35/00 |
| | | | | 424/1.69 |
| 2010/0215582 | A1* | 8/2010 | Isoda | ........... A61K 8/416 |
| | | | | 424/9.1 |

FOREIGN PATENT DOCUMENTS

| | | | | |
|---|---|---|---|---|
| JP | 01299299 | * | 12/1989 | ........... C07K 7/10 |
| WO | WO2007041596 A2 | * | 4/2007 | ........... G01N 33/53 |

OTHER PUBLICATIONS

Usui et al. A novel array format for monitoring cellular uptake using a photo-cleavable linker for peptide release. Chem. Commun. 2013; 49: 6394-6396. (Year: 2013).*
Takeshima et al. Translocation of Analogues of the Antimicrobial Peptides Magainin and Buforin across Human Cell Membranes. J Biol Chem . Jan. 10, 2003;278(2): 1310-5. (Year: 2003).*
Resnick et al. A Novel Endopeptidase from Xenopus That Recognizes a-Helical Secondary Structure. Cell 1991, 66: 541-554. (Year : 1991).*
STN. CAS REGISTRYSM: Exact and pattern searching of protein sequences. Nov. 2008. (Year: 2008).*

* cited by examiner

*Primary Examiner* — Soren Harward
*Assistant Examiner* — Jia-Hai Lee

(57) ABSTRACT

Disclosed herein are novel synthetic polypeptides and uses thereof in the preparation of liposomes. According to embodiments of the present disclosure, the synthetic polypeptide comprises a membrane lytic motif, a masking motif, and a linker configured to link the membrane lytic motif and the masking motif. The linker is cleavable by a stimulus, such as, light, protease, or phosphatase. Once being coupled to a liposome, the exposure to the stimulus cleaves the linker that results in the separation of the masking motif from the membrane lytic motif, which in turn exerts membrane lytic activity on the liposome that leads to the collapse of the intact structure of the liposome, and releases the agent encapsulated in the liposome to the target site. Also disclosed herein are methods of diagnosing or treating a disease in a subject by use of the present liposomes.

7 Claims, 18 Drawing Sheets

Specification includes a Sequence Listing.

```
                        SEQUENCE LISTING

<160> NUMBER OF SEQ ID NOS: 26

<210> SEQ ID NO 1
<211> LENGTH: 23
<212> TYPE: PRT
<213> ORGANISM: Artificial Sequence
<220> FEATURE:
<223> OTHER INFORMATION: synthesized-full length-Magainin 2

<400> SEQUENCE: 1

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 2
<211> LENGTH: 17
<212> TYPE: PRT
<213> ORGANISM: Artificial Sequence
<220> FEATURE:
<223> OTHER INFORMATION: synthesized Magainin 2

<400> SEQUENCE: 2

Gly Ile Gly Lys Phe Leu His Ser Ala Lys Lys Phe Gly Lys Ala Phe
1               5                   10                  15

Val

<210> SEQ ID NO 3
<211> LENGTH: 17
<212> TYPE: PRT
<213> ORGANISM: Artificial Sequence
<220> FEATURE:
<223> OTHER INFORMATION: synthesized mutant Magainin 2

<400> SEQUENCE: 3

Gly Ile Gly Lys Phe Leu His Ser Ala Lys Lys Trp Gly Lys Ala Phe
1               5                   10                  15

Val

<210> SEQ ID NO 4
<211> LENGTH: 26
<212> TYPE: PRT
<213> ORGANISM: Artificial Sequence
<220> FEATURE:
<223> OTHER INFORMATION: synthesized Melittin

<400> SEQUENCE: 4

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 5
<211> LENGTH: 24
<212> TYPE: PRT
<213> ORGANISM: Artificial Sequence
<220> FEATURE:
<223> OTHER INFORMATION: synthesized mutant Melittin
```

```
<400> SEQUENCE: 5

Gly Ile Gly Ala Val Leu Lys Val Leu Thr Arg Gly Leu Pro Ala Leu
1               5                   10                  15

Ile Lys Trp Ile Lys Thr Ser Arg
            20

<210> SEQ ID NO 6
<211> LENGTH: 21
<212> TYPE: PRT
<213> ORGANISM: Artificial Sequence
<220> FEATURE:
<223> OTHER INFORMATION: synthesized Pexiganan

<400> SEQUENCE: 6

Gly Ile Gly Lys Phe Leu Lys Lys Ala Lys Lys Phe Gly Lys Ala Phe
1               5                   10                  15

Val Lys Ile Leu Lys
            20

<210> SEQ ID NO 7
<211> LENGTH: 21
<212> TYPE: PRT
<213> ORGANISM: Artificial Sequence
<220> FEATURE:
<223> OTHER INFORMATION: synthesized EP1

<400> SEQUENCE: 7

Gly Phe Ile Phe His Ile Ile Lys Gly Leu Phe His Ala Gly Lys Met
1               5                   10                  15

Ile His Gly Leu Val
            20

<210> SEQ ID NO 8
<211> LENGTH: 17
<212> TYPE: PRT
<213> ORGANISM: Artificial Sequence
<220> FEATURE:
<223> OTHER INFORMATION: synthesized Magainin 2-3pY
<220> FEATURE:
<221> NAME/KEY: MOD_RES
<222> LOCATION: 5,12,16
<223> OTHER INFORMATION: phosphorylated Y residue
      PHOSPHORYLATION

<400> SEQUENCE: 8

Gly Ile Gly Lys Tyr Leu His Ser Ala Lys Lys Tyr Gly Lys Ala Tyr
1               5                   10                  15

Val

<210> SEQ ID NO 9
<211> LENGTH: 17
<212> TYPE: PRT
<213> ORGANISM: Artificial Sequence
<220> FEATURE:
<223> OTHER INFORMATION: synthezied Magainin 2-2pY
<220> FEATURE:
<221> NAME/KEY: MOD_RES
<222> LOCATION: 5,16
<223> OTHER INFORMATION: phosphorylated Y residue
      PHOSPHORYLATION

<400> SEQUENCE: 9

Gly Ile Gly Lys Tyr Leu His Ser Ala Lys Lys Trp Gly Lys Ala Tyr
1               5                   10                  15
```

Val

```
<210> SEQ ID NO 10
<211> LENGTH: 17
<212> TYPE: PRT
<213> ORGANISM: Artificial Sequence
<220> FEATURE:
<223> OTHER INFORMATION: synthesized Magainin 2-2pS
<220> FEATURE:
<221> NAME/KEY: MOD_RES
<222> LOCATION: 8,15
<223> OTHER INFORMATION: phosphorylated S residue
      PHOSPHORYLATION

<400> SEQUENCE: 10

Gly Ile Gly Lys Phe Leu His Ser Ala Lys Lys Trp Gly Lys Ser Phe
1               5                   10                  15

Val

<210> SEQ ID NO 11
<211> LENGTH: 24
<212> TYPE: PRT
<213> ORGANISM: Artificial Sequence
<220> FEATURE:
<223> OTHER INFORMATION: synthesized Melittin mutation-2pY
<220> FEATURE:
<221> NAME/KEY: MOD_RES
<222> LOCATION: 9,16
<223> OTHER INFORMATION: phosphorylated Y residue
      PHOSPHORYLATION

<400> SEQUENCE: 11

Gly Ile Gly Ala Val Leu Lys Val Tyr Thr Arg Gly Leu Pro Ala Tyr
1               5                   10                  15

Ile Lys Trp Ile Lys Thr Ser Arg
            20

<210> SEQ ID NO 12
<211> LENGTH: 21
<212> TYPE: PRT
<213> ORGANISM: Artificial Sequence
<220> FEATURE:
<223> OTHER INFORMATION: synthesized EP1-2pY
<220> FEATURE:
<221> NAME/KEY: MOD_RES
<222> LOCATION: 10,13
<223> OTHER INFORMATION: phosphorylated Y residue
      PHOSPHORYLATION

<400> SEQUENCE: 12

Gly Phe Ile Phe His Ile Ile Lys Gly Tyr Phe His Tyr Gly Lys Met
1               5                   10                  15

Ile His Gly Leu Val
            20

<210> SEQ ID NO 13
<211> LENGTH: 17
<212> TYPE: PRT
<213> ORGANISM: Artificial Sequence
<220> FEATURE:
<223> OTHER INFORMATION: synthesized Magainin 2-pY
<220> FEATURE:
<221> NAME/KEY: MOD_RES
<222> LOCATION: 12
<223> OTHER INFORMATION: phosphorylated Y residue
      PHOSPHORYLATION

<400> SEQUENCE: 13
```

```
Gly Ile Gly Lys Phe Leu His Ser Ala Lys Tyr Gly Lys Ala Phe
1               5                   10                  15

Val

<210> SEQ ID NO 14
<211> LENGTH: 17
<212> TYPE: PRT
<213> ORGANISM: Artificial Sequence
<220> FEATURE:
<223> OTHER INFORMATION: synthesized Magainin 2-pS
<220> FEATURE:
<221> NAME/KEY: MOD_RES
<222> LOCATION: 8
<223> OTHER INFORMATION: phosphorylated S residue
      PHOSPHORYLATION

<400> SEQUENCE: 14

Gly Ile Gly Lys Phe Leu His Ser Ala Lys Lys Trp Gly Lys Ala Phe
1               5                   10                  15

Val

<210> SEQ ID NO 15
<211> LENGTH: 17
<212> TYPE: PRT
<213> ORGANISM: Artificial Sequence
<220> FEATURE:
<223> OTHER INFORMATION: synthesized Scrambled Magainin 2

<400> SEQUENCE: 15

Lys Phe Trp His Ala Lys Gly Gly Gly Ser Phe Ile Ala Lys Val Lys
1               5                   10                  15

Leu

<210> SEQ ID NO 16
<211> LENGTH: 13
<212> TYPE: PRT
<213> ORGANISM: Artificial Sequence
<220> FEATURE:
<223> OTHER INFORMATION: synthesized Temporin L

<400> SEQUENCE: 16

Phe Val Gln Trp Phe Ser Lys Phe Leu Gly Arg Ile Leu
1               5                   10

<210> SEQ ID NO 17
<211> LENGTH: 26
<212> TYPE: PRT
<213> ORGANISM: Artificial Sequence
<220> FEATURE:
<223> OTHER INFORMATION: synthesized TP4

<400> SEQUENCE: 17

Gly Phe Ile His His Ile Ile Gly Gly Leu Phe Ser Ala Gly Lys Ala
1               5                   10                  15

Ile His Arg Leu Ile Arg Arg Arg Arg Arg
                20                  25

<210> SEQ ID NO 18
<211> LENGTH: 37
<212> TYPE: PRT
<213> ORGANISM: Artificial Sequence
<220> FEATURE:
<223> OTHER INFORMATION: synthesized LL37

<400> SEQUENCE: 18
```

```
Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
                20                  25                  30

Pro Arg Thr Glu Ser
            35

<210> SEQ ID NO 19
<211> LENGTH: 21
<212> TYPE: PRT
<213> ORGANISM: Artificial Sequence
<220> FEATURE:
<223> OTHER INFORMATION: synthesized Buforin II

<400> SEQUENCE: 19

Thr Arg Ser Ser Arg Ala Gly Leu Gln Phe Pro Val Gly Arg Val His
1               5                   10                  15

Arg Leu Leu Arg Lys
            20

<210> SEQ ID NO 20
<211> LENGTH: 20
<212> TYPE: PRT
<213> ORGANISM: Artificial Sequence
<220> FEATURE:
<223> OTHER INFORMATION: synthesized Ranalexin

<400> SEQUENCE: 20

Phe Leu Gly Gly Leu Ile Lys Ile Val Pro Ala Met Ile Cys Ala Val
1               5                   10                  15

Thr Lys Lys Cys
            20

<210> SEQ ID NO 21
<211> LENGTH: 12
<212> TYPE: PRT
<213> ORGANISM: Artificial Sequence
<220> FEATURE:
<223> OTHER INFORMATION: synthesized Bactenecin 1

<400> SEQUENCE: 21

Arg Leu Cys Arg Ile Val Val Ile Arg Val Cys Arg
1               5                   10

<210> SEQ ID NO 22
<211> LENGTH: 21
<212> TYPE: PRT
<213> ORGANISM: Artificial Sequence
<220> FEATURE:
<223> OTHER INFORMATION: synthesized Thanatin

<400> SEQUENCE: 22

Gly Ser Lys Lys Pro Val Pro Ile Ile Tyr Cys Asn Arg Arg Thr Gly
1               5                   10                  15

Lys Cys Gln Arg Met
            20

<210> SEQ ID NO 23
<211> LENGTH: 8
<212> TYPE: PRT
<213> ORGANISM: Artificial Sequence
<220> FEATURE:
<223> OTHER INFORMATION: synthesized linker

<400> SEQUENCE: 23
```

-continued

```
Ser Pro Ala Tyr Tyr Thr Ala Ala
1               5

<210> SEQ ID NO 24
<211> LENGTH: 6
<212> TYPE: PRT
<213> ORGANISM: Artificial Sequence
<220> FEATURE:
<223> OTHER INFORMATION: synthesized linker

<400> SEQUENCE: 24

Pro Leu Gly Val Arg Gly
1               5

<210> SEQ ID NO 25
<211> LENGTH: 13
<212> TYPE: PRT
<213> ORGANISM: Artificial Sequence
<220> FEATURE:
<223> OTHER INFORMATION: synthesized Melittin_X2 sequence

<400> SEQUENCE: 25

Val Leu Thr Thr Gly Leu Pro Ala Leu Ile Ser Trp Ile
1               5                   10

<210> SEQ ID NO 26
<211> LENGTH: 4
<212> TYPE: PRT
<213> ORGANISM: Artificial Sequence
<220> FEATURE:
<223> OTHER INFORMATION: synthesized Melittin_X1 sequence

<400> SEQUENCE: 26

Lys Arg Lys Arg
1
```

SYNTHETIC POLYPEPTIDES AND USES THEREOF

CROSS-REFERENCE TO RELATED APPLICATIONS

This application relates to and claims the benefit of U.S. Provisional Application No. 62/691,145, filed Jun. 28, 2018; the content of the application is incorporated herein by reference in its entirety.

BACKGROUND OF THE INVENTION

1. Field of the Invention

The present disclosure in general relates to the field of disease treatment. More particularly, the present disclosure relates to synthetic polypeptides and their uses in the preparation of liposomes for treating diseases.

2. Description of Related Art

Liposome, a spherical vesicle comprising at least one lipid bilayer for encapsulating an aqueous core, is recognized as one of the most consequential carriers in the history of chemotherapeutic drug delivery systems. Compared with free drugs, drugs encapsulated by liposomes may result in better biodistribution in desired tissues or organs via the enhanced permeability retention (EPR) effect. Current liposomes are mostly composed by saturated lipids, which form a stable membrane for the encapsulation of therapeutic drugs. These liposomes follow non-Fick's release behaviour (i.e., no early-stage diffusional release) so that healthy tissues can be protected when highly toxic drugs (e.g., chemotherapeutics) are loaded in the aqueous core of the liposome. However, the non-Fick's release property is a two-edged sword. Although it protects healthy tissues, it also makes the liposomal drugs less bioavailable. The highly mechanical strength requirement for liposome stability for long blood circulation time actually hurdles the liposomal release, and make the liposomal drugs safer but less effective. In general, conventional liposomes although are stable, they release drugs passively, and often too slow, incomplete and poorly controlled. To overcome this dilemma, fast-reacting but stable trigger-responsive liposome vesicle design is needed to be improved the liposomal drug efficacy while keeping its original safety features. Smart liposomes, which may be rapidly trigger-release at intended sites, provide a potential means to avoid slow and incomplete passive drug leakage, and are less likely to produce prolonged low dose drug exposure that relates to the development of drug resistance.

Triggered release is one of the major focuses of research for clinical applications of liposome. A variety of stimuli-responsive liposomes have been exploited to trigger the release of liposomal content upon exposure to the triggering signal, for example, temperature, pH, light, enzyme, near-infrared, ultrasound, redox potential, and magnetic field. Most of the stimuli-responsive liposomes are composed by a relatively high percentage of unnatural synthetic lipids as a switch to facilitate the release. However, the employment of unnatural lipids in liposome raises toxicity concerns for translational medicine. Peptides, on the other hand, provide an alternative choice to equip liposome with trigger-release function based on the biocompatibility and effective membrane activity thereof. Unfortunately, despite great interest and considerable efforts for the past decades, peptidyl liposome approaches have not yet initiated to generate a satisfactory trigger-responsive liposome. Up to the present time, there is no trigger-responsive membranolytic peptide suitable to be anchored to liposomal surface, that responses to light or disease related enzymatic signal, without premature release.

In view of the foregoing, there exists in the related art a need for an improved stimuli-responsive liposome for releasing therapeutic drugs encapsulated therein in a safer and more precision manner.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to a synthetic polypeptide, which comprises a membrane lytic motif, a masking motif, and a linker configured to link the membrane lytic motif and the masking motif.

According to embodiments of the present disclosure, the membrane lytic motif comprises 14-30 amino acid residues, wherein the number of hydrophobic amino acid residues in the membrane lytic motif is 5-10; the number of positive-charged amino acid residues in the membrane lytic motif is 4-10; and the number of negative-charged amino acid residues in the membrane lytic motif is equal to or less than 1. In the case when the amino acid residues are aligned into an alpha-helix having a plurality of repeats, each repeat includes 7 amino acid residues, and has a first turn and a second turn, wherein the first turn has 4 amino acid residues, and the second turn has 3 amino acid residues. Basically, the alignment of the amino acid resides in each repeat is performed in accordance with the position numbers, in sequence, as depicted in FIG. 1, wherein the amino acid residues in the first turn are designated as positions 1-4, and the amino acid residues in the second turn are designated as positions 5-7. The same position number in each repeats of the alpha-helix forms a corresponding site. The number of the corresponding site comprising one or more of the positive-charged amino acid residue in the membrane lytic motif is 3 or 4, and at least two of the corresponding sites comprising one or more of the positive-charged amino acid residue are adjacent to each other.

The masking motif is a peptide comprising at least 10 negative-charged amino acid residues, or is a phosphoryl group. The linker is a photocleavable or protease-cleavable moiety, or is a phosphoester bond.

According to certain embodiments of the present disclosure, the masking motif is the peptide, and the linker is the photocleavable or the protease-cleavable moiety. The photocleavable moiety may have the structure of formula (I) or formula (II):

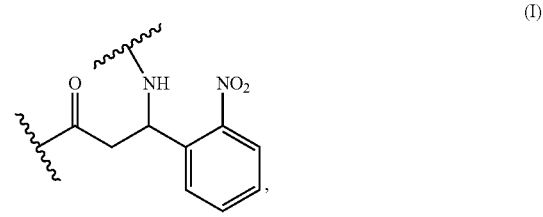

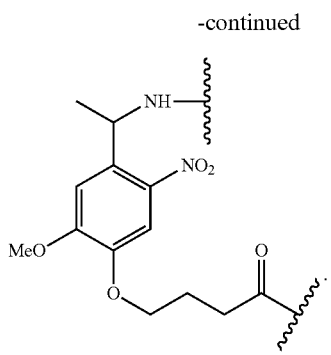
(II)

Regarding the protease-cleavable moiety, it is an amino acid sequence that is cleavable by matrix metalloproteinase (MMP), or cathepsin. In some specific examples, the linker is a peptide comprising the amino acid sequence of SEQ ID NO: 23 or 24. In one specific example, the linker is a valine-citrulline (VC) dipeptide residue.

According to some embodiments of the present disclosure, the masking motif is the phosphoryl group. In these embodiments, the linker is the phosphoester bond, which is cleavable by phosphatase, and is formed between the phosphoryl group, and any of the serine (S), tyrosine (Y) or threonine (T) residue of the membrane lytic motif, wherein the number of the S, Y and/or T residues having the phosphoryl group linked thereto is at least 2, and the corresponding site comprising one or more S, Y and/or T residues having the phosphoryl group linked thereto is different from the corresponding site comprising one or more of the positive-charged amino acid residue.

In general, the hydrophobic amino acid residue is leucine (L), isoleucine (I), valine (V), phenylalanine (F), tryptophan (W), or tyrosine (Y); the negative-charged amino acid residue is aspartate (D), or glutamate (E); and the positive-charged amino acid residue is lysine (K), arginine (R), or histidine (H).

According to certain embodiments of the present disclosure, the membrane lytic motif comprises the amino acid sequence of $(X_1)_{1-4}(X_2)_{1-13}(X_1)_{1-4}$, wherein each $X_1$ is independently selected from the group consisting of, lysine (K), arginine (R) and histidine (H) residues, and each $X_2$ is independently selected from the group consisting of serine (S), threonine (T), asparagine (N), glutamine (Q), cysteine (C), glycine (G), proline (P), alanine (A), valine (V), isoleucine (I), leucine (L), methionine (M), phenylalanine (F), tyrosine (Y), tryptophan (W), aspartate (D), and glutamate (E) residues. Preferably, each $X_2$ is independently selected from the group consisting of serine, threonine, asparagine, glutamine, cysteine, glycine, proline, alanine, valine, isoleucine, leucine, methionine, phenylalanine, tyrosine, and tryptophan residues.

In some working examples of the present disclosure, the membrane lytic motif comprises any of the amino acid sequences of SEQ ID NOs: 1-12.

According to some embodiments of the present disclosure, the masking motif of the present synthetic polypeptide comprises at least 10 negative-charged amino acid residues (i.e., the aspartate and/or glutamate residues). According to certain examples of the present disclosure, the masking motif comprises at least 10 glutamate residues. In one specific example, the masking motif consists of 12 glutamate residues.

Another aspect of the present disclosure pertains to the use of the present synthetic polypeptide in the preparation of a liposome. In structure, the liposome comprises a center core; a lipid layer encapsulating the center core; and a synthetic polypeptide of the present disclosure coupled to the lipid layer.

The center core may comprise a therapeutic agent or a reporter molecule. Depending on desired purposes, the therapeutic agent may be an anti-tumor agent, an anti-inflammatory agent, an anti-microbial agent, an anti-oxidant agent, a growth factor, a neuron transmitter, or a protein inhibitor. The reporter molecule may be a contrast agent, or a fluorescent molecule.

Also disclosed herein are methods for diagnosing or treating a disease in a subject. The method for diagnosing a disease comprises administering to the subject an effective amount of the present liposome, which comprises a reporter molecule in the center core. For the purposes of treating a disease in a subject, an effective amount of the present liposome, which comprises a therapeutic agent in the center core, is administered to the subject so as to ameliorate or alleviate the symptoms associated with the disease.

The subject of the present method is a mammal; preferably, a human.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where:

FIG. 2G) according to another embodiment of the present disclosure.

FIG. 4A: Dot plot of release percentage versus irradiation time, exhibiting that only 3 minute UV exposure was needed to induce effective release. FIG. 4B: Dot plot of liposomal zeta-potential versus irradiation time, also suggesting that only 3 minute UV exposure was needed to photolytically remove the poly-glutamate trigger-responsive masking motif. FIG. 4C: Dot plot of post-irradiation incubation time needed versus release percentage, exhibiting that 30 minutes of post-irradiation incubation was needed to fully unload the liposomal DOX. FIG. 4D: Histogram of the peptide substitution level versus the release percentage, exhibiting that 1-MDL at peptide/lipid ratio=1/300 possessed the maximal content release after irradiation. DDL: the DOX-loaded liposome coupling with dithiothreitol (DTT); 1-MDL: the DOX-loaded liposome coupling with photo-responsive Magainin 2 (W12) (peptide 1); 2-MDL: the DOX-loaded liposome coupling with photo-responsive scrambled Magainin 2 (peptide 2). DDL and 2-MDL served as the negative controls of the instant experiment.

FIG. 12A: $T_1$-weighted relaxation rate at TR=550 ($S_0$ is the initial signal of liposomes before trigger activation, and $S_{max}$ is the maximal signal of complete-released $Gd^{3+}$-DTPA liposome by addition of 1% Triton™-X100). FIG. 12B: $T_1$-map of $Gd^{3+}$-DTPA liposomes (To is the initial relaxation time of liposomes before trigger activation, and $T_{max}$ is the maximal relaxation rate of complete-released $Gd^{3+}$-DTPA liposome by addition of 1% Triton™-X100) in presence or absence of light irradiation followed by 1 hour at 37° C. incubation. The white box indicates the signal change after light irradiation in 1-MGL.

Figure 1:
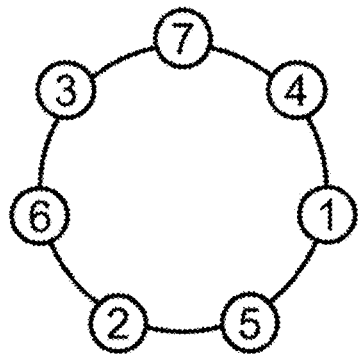
FIG. 1 is a helical wheel diagram depicting the alignment of amino acid sequence in each helical repeat of the membrane lytic motif according to one embodiment of the present disclosure.

In accordance with common practice, the various described features/elements are not drawn to scale but instead are drawn to best illustrate specific features/elements relevant to the present invention. Also, like reference numerals and designations in the various drawings are used to indicate like elements/parts.

DETAILED DESCRIPTION OF THE INVENTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The terms "peptide," "polypeptide" and "protein" are used interchangeably herein, and refer to a polymer of amino acids without regard to the length of the polymer. This term also does not specify or exclude chemical or post-expression modifications of the polypeptides of the invention, although chemical or post-expression modifications of these polypeptides may be included or excluded as specific embodiments. Throughout the present disclosure, the positions of any specified amino acid residues within a polypeptide are numbered starting from the N terminus of the polypeptide.

When amino acids are not designated as either D- or L-amino acids, the amino acid is either an L-amino acid or could be either a D- or L-amino acid, unless the context requires a particular isomer. Further, the notation used herein for the polypeptide amino acid residues are those abbreviations commonly used in the art.

As used herein, the term "synthetic polypeptide" refers to a polypeptide which does not comprise an entire naturally occurring molecule. The polypeptide is "synthetic" in that it may be produced by human intervention using such techniques as chemical synthesis, recombinant genetic techniques, or fragmentation of whole antigen or the like.

The term "motif" as used herein refers to a portion of the synthetic polypeptide of the present disclosure. Specifically, the term "motif" as used herein refers to an amino acid sequence, or a chemical group (e.g., a phosphoryl group). Preferably, said amino acid sequence has at least 10 amino acid residues in length.

As used herein, the term "moiety" is used as understood by those skilled in the art, and refers to a part of a molecule, a molecular fragment, or a polymer, for example, a portion of an amino acid residue, peptide, or compound.

The term "alpha-helix" (α-helix) or "alpha-helical structure" is understood to be a secondary structure arrangement of a polypeptide, in which the amino acid residues of the polypeptide interact with a particular hydrogen bonding pattern, and thus define a helical structure. For example, the hydrogen bonding pattern in a standard alpha-helix is between the carbonyl oxygen of a residue in position "n," and the amide hydrogen of another residue in the "n+4" position. For the 310-helix, hydrogen bond is independently formed between residues in positions of "n" and "n+3". For a pi-helix (π-helix), hydrogen bond is independently formed between residues in positions "n" and "n+5." The number of residues per turn in each alpha-helix is independently about 3.6, 3.0 and 4.4 for the standard alpha-helix, 310-helix, and pi-helix. The alpha-helix may have a right- or left-handed coiled conformation. As used herein, the terms "turn" and "helical turn" are used interchangeably, and refer to the single circle in the helical structure.

The term "helical wheel diagram" is understood to mean any type of plot or visual representation used to illustrate the properties of alpha helices in polypeptides. Typically, the amino acid sequence of the polypeptide is plotted in a rotating manner where the angle of rotation between consecutive amino acids is about 100°, so that the final representation looks down the helical axis.

Here, the term "couple", "link" and "conjugate" are interchangeably used, and refers to any means of connecting two components either via direct linkage or via indirect linkage between two components.

The term "administered" or "administering" are used interchangeably herein to refer a mode of delivery, including, without limitation, intravenously, intramuscularly, intraperitoneally, intraarterially, intracranially, or subcutaneously administering an agent (e.g., the liposome) of the present invention.

The term "diagnosis" as used herein refers to methods by which the skilled artisan can estimate and/or determine the probability ("a likelihood") of whether or not a patient is suffering from a given disease, disorder, or condition. The term "diagnosis" also encompasses detecting a predisposition to a disease, disorder, or condition, determining the therapeutic effect of a drug therapy, or predicting the pattern of response to a drug therapy. The diagnostic methods of the present invention may be used independently, or in combination with other diagnostic and/or staging methods known in the medical art for a particular disease, disorder, or condition. That such a diagnosis is "determined" is not meant to imply that the diagnosis is 100% accurate.

"Treatment" as used herein includes preventative (e.g., prophylactic), curative or palliative treatment of a disease in a mammal, particularly human; and includes: (1) preventative (e.g., prophylactic), curative or palliative treatment of a disease or condition (e.g., a cancer) from occurring in an individual who may be pre-disposed to the disease but has not yet been diagnosed as having it; (2) inhibiting a disease (e.g., by arresting its development); or (3) relieving a disease (e.g., reducing symptoms associated with the disease).

The term "effective amount" as referred to herein designate the quantity of a component which is sufficient to yield a desired response. For therapeutic purposes, the effective amount is also one in which any toxic or detrimental effects of the component are outweighed by the therapeutically beneficial effects. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two, or more doses in a suitable form to be administered at one, two or more times throughout a designated time period. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in grams, milligrams or micrograms or as milligrams per kilogram of body weight (mg/Kg). Alternatively, the effective amount can be expressed in the concentration of the active component (e.g., the liposome of the present disclosure), such as molar concentration, mass concentration, volume concentration, molality, mole fraction, mass fraction and mixing ratio. Persons having ordinary skills could calculate the human equivalent dose (HED) for the medicament (such as the present liposome) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

The term "subject" refers to a mammal including the human species that is treatable with the liposome and/or method of the present invention. The term "subject" is intended to refer to both the male and female gender unless one gender is specifically indicated.

II. Description of the Invention

The present disclosure aims at providing a stimuli-responsive liposome for diagnosing or treating diseases in a safer and more accurate manner. The stimuli-responsive liposome is characterized in having specific polypeptide coupled to and/or in the lipid layer. The polypeptide is cleavable by a stimulus that results in the destruction of the liposome thereby achieving targeted delivery and/or controlled release (CR) of diagnostic or therapeutic agents.

Thus, the first aspect of the present disclosure is directed to a synthetic polypeptide, which is redesigned and chemically modified from a naturally occurred antimicrobial polypeptide. The synthetic polypeptide comprises a membrane lytic motif, a masking motif, and a linker configured to link the membrane lytic motif and the masking motif.

The membrane lytic motif comprises 14-30 amino acid residues, in which the number of hydrophobic amino acid residues (i.e., the leucine, isoleucine, valine, phenylalanine, tryptophan, and/or tyrosine residues) in the membrane lytic motif is 5-10; the number of positive-charged amino acid residues (i.e., the lysine, arginine, and/or histidine residues) in the membrane lytic motif is 4-10; and the number of negative-charged amino acid residues (i.e., the aspartate and/or glutamate residues) in the membrane lytic motif is equal to or less than 1.

The membrane lytic motif of the present synthetic polypeptide is characterized in having specific properties when aligning into an alpha-helical structure. Specifically, when the amino acid sequence of the membrane lytic motif is aligned into an alpha-helical structure with a heptad repeat occurring every two turns of the helix, the first helical turn has four amino acid residues, and the second helical turn has three amino acid residues. The four amino acid residues of the first helical turn are respectively designated as positions 1-4, and the three amino acid residues of the second helical turn are respectively designated as positions 5-7. For better illustration and understanding, the positions 1-7 in each repeat may be represented by a helical wheel diagram as illustrated in FIG. 1, in which the alignment of the amino acid sequence in each repeat is performed in accordance with the position numbers, in sequence (i.e., from position 1 to position 7). The same position number in each repeats of the alpha-helix forms a corresponding site. According to embodiments of the present disclosure, the number of the corresponding site comprising one or more of the positive-charged amino acid residue (i.e., the lysine, arginine, and/or histidine residues) in the membrane lytic motif is 3 or 4, and at least two of the corresponding sites comprising the positive-charged amino acid residue(s) are adjacent to each other.

Figure 2A:
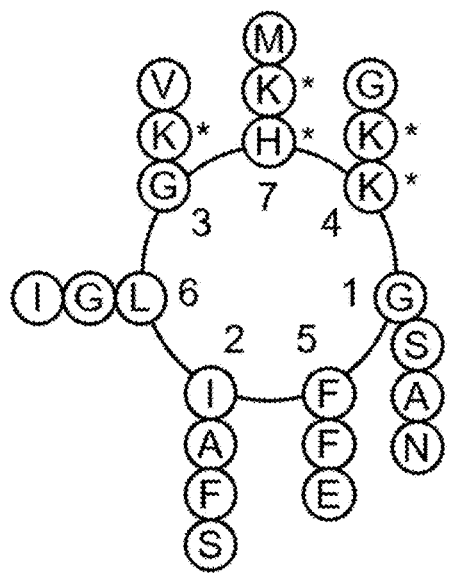
FIGS. 2A to 2G are helical wheel diagrams respectively depicting the alignments of membrane lytic motif of the present polypeptide, including Magainin 2 (FIG. 2A), truncated Magainin 2 (FIG. 2B), mutant Magainin 2 (FIG. 2C), Melittin (FIG. 2D), mutant Melittin (FIG. 2E), Pexiganan (FIG. 2F), and Epinecidin-1 (EP1.

Several examples of the present membrane lytic motif are provided in detailed below. Reference is first made to FIG. 2A, in which the alpha-helical structure of Magainin 2 (SEQ ID NO: 1) is projected on a helical wheel diagram. According to FIG. 2A, the alpha-helical structure of Magainin 2 has 4 repeats, in which the first repeat comprises the amino acid residues of G, I, G, K, F, L, H, from positions 1 to 7; the second repeat comprises the amino acid residues of S, A, K, K, F, G, K, from positions 1 to 7; the third repeat comprises the amino acid residues of A, F, V, G, E, I, M, from positions 1 to 7; and the fourth repeat comprises amino acid residues of N and S, respectively at positions 1 and 2. The positive-charged amino acid residues (i.e., the lysine, arginine, and/or histidine residues) are marked by symbol "*" in FIG. 2A. The amino acid residues of G, S, A, N at position 1 are taken together to form a corresponding site 1. Similarly, the amino acid residues of I, A, F, S at position 2 are taken together to form a corresponding site 2; while the amino acid residues of G, K, V at position 3 are taken together to form a corresponding site 3; and so on. As depicted in FIG. 2A, the number of the corresponding site comprising positive-charged amino acid residue(s) is 3, which are the corresponding sites 3, 4, and 7. Specifically, the corresponding site 3 has 1 positive-charged amino acid residue, whereas each of the corresponding sites 4 and 7 has 2 positive-charged amino acid residues. Further, the three corresponding sites 3, 4 and 7 are adjacent to each other in the helical wheel diagram. In the case when the membrane lytic motif is Magainin 2 as illustrated in FIG. 2A, then the masking motif (e.g., the peptide comprising at least 10 glutamate residues) is linked to the C-terminus of the serine (S) residue at the corresponding site 2 of the membrane lytic motif via the linker.

Figure 2B:
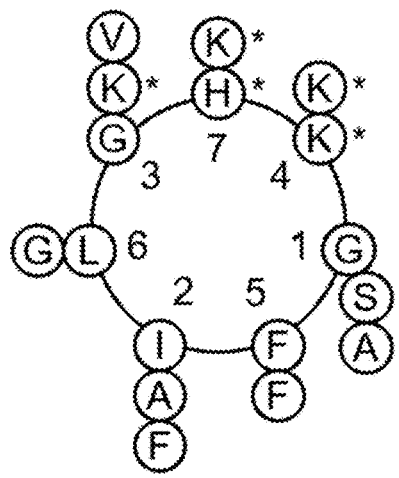
Figure 2C:
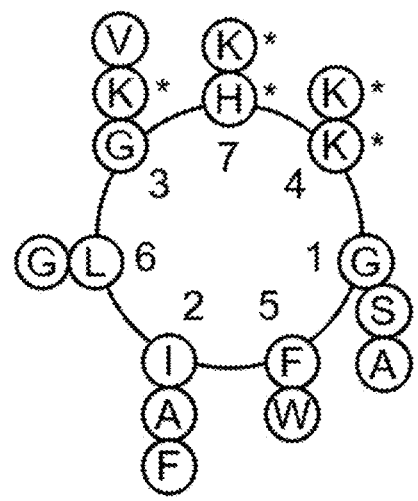

Alternative examples of the present membrane lytic motif are provided in FIGS. 2B and 2C, which respectively depict the helical wheel diagram of the truncated form of Magainin 2 (SEQ ID NO: 2) and the mutant form of Magainin 2 (SEQ ID NO: 3). The amino acid sequence alignments in FIGS. 2B and 2C are quite similar to that of FIG. 2A, and hence, detailed description thereof is omitted herein for the sake of brevity. According to FIGS. 2B and 2C, both the truncated Magainin 2 and the mutant Magainin 2 have 3 adjacent corresponding sites (i.e., the corresponding sites 3, 4 and 7), which respectively comprise 1, 2 and 2 positive-charged amino acid residues. In the example where the membrane lytic motif is the truncated Magainin 2 of FIG. 2B, or the mutant form of Magainin 2 of FIG. 2C, then the masking motif is linked to the C-terminus of the valine (V) residue at the corresponding site 3 of the membrane lytic motif via the linker.

Figure 2D:
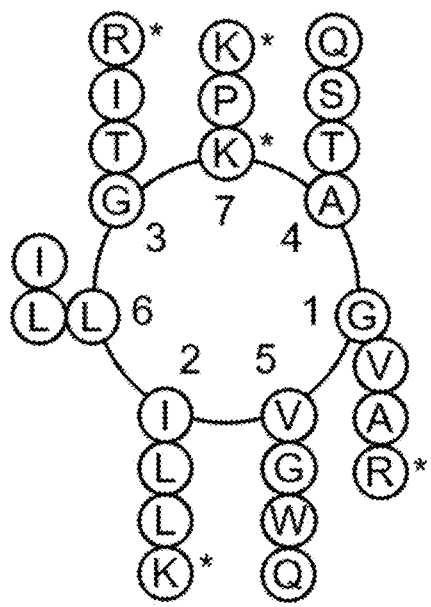
Figure 2E:
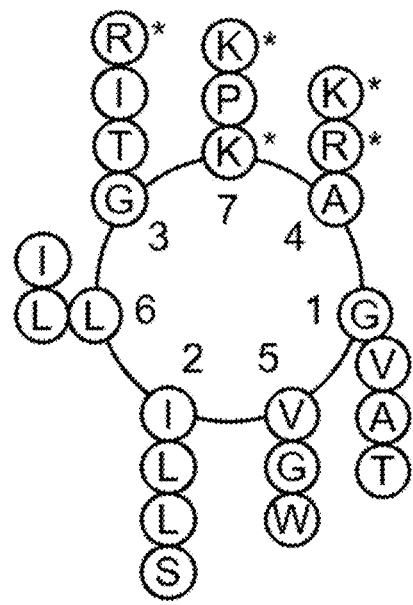

Exemplified membrane lytic motif of the present invention includes Melittin (SEQ ID NO: 4) and its mutant form (SEQ ID NO: 5). As depicted in FIG. 2D, there are 4 corresponding sites in the helical wheel diagram of Melittin, i.e., the corresponding sites 1, 2, 3, and 7, respectively comprising 1, 1, 1 and 2 positive-charged amino acid residue(s), and the corresponding sites 3 and 7 are adjacent to each other. Similarly, there are 3 corresponding sites in the helical wheel diagram of the mutant Melittin, i.e., the corresponding sites 3, 4, and 7, which are adjacent to one another and respectively comprise 1, 2, and 2 positive-charged amino acid residue(s) (FIG. 2E). When the membrane lytic motif is the Melittin of FIG. 2D, then the masking motif is linked to the C-terminus of the glutamine (Q) residue at the corresponding site 5 of the membrane lytic motif via the linker. Alternatively, in the case when the membrane lytic motif is the mutant Melittin of FIG. 2E, then the masking motif is linked to the C-terminus of the arginine (R) residue at the corresponding site 3 of the membrane lytic motif via the linker.

Figure 2F:
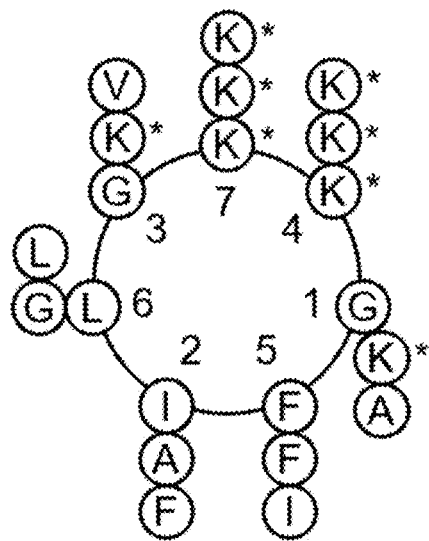

Another exemplified membrane lytic motif is Pexiganan (SEQ ID NO: 6), the helical wheel diagram of which is depicted in FIG. 2F. In this embodiment, Pexiganan has 4 corresponding sites, i.e., the corresponding sites 1, 3, 4, and 7, which respectively comprise 1, 1, 3, and 3 positive-charged amino acid residue(s), and the corresponding sites 3, 4, and 7 are adjacent to each other. In the example where the membrane lytic motif is the Pexiganan of FIG. 2F, then the masking motif is linked to the C-terminus of the lysine (K) residue at the corresponding site 7 of the membrane lytic motif via the linker.

Figure 2G:
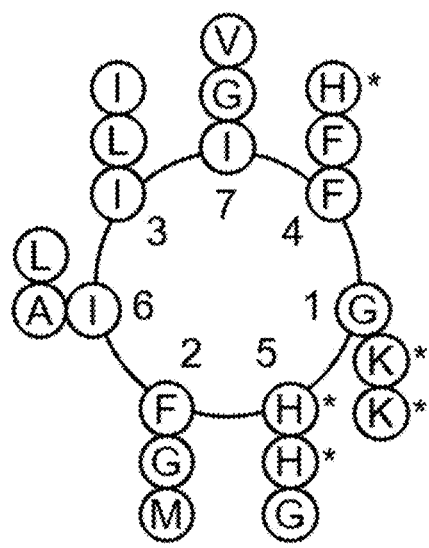
Figure 3A:
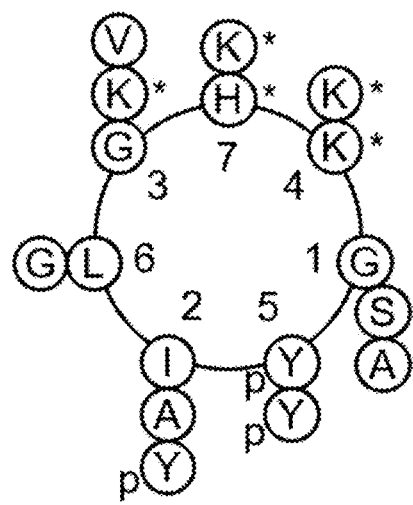
FIGS. 3A to 3E are helical wheel diagrams respectively depicting the alignments of membrane lytic motif masked by phosphoryl groups, in which the membrane lytic motif includes Magainin 2-3pY (FIG. 3A), Magainin 2-2pY (FIG. 3B), Magainin 2-2pS (FIG. 3C), mutant Melittin-2pY (FIG. 3D), and EP1-2pY (FIG. 3E) according to another embodiment of the present disclosure.
Figure 3B:
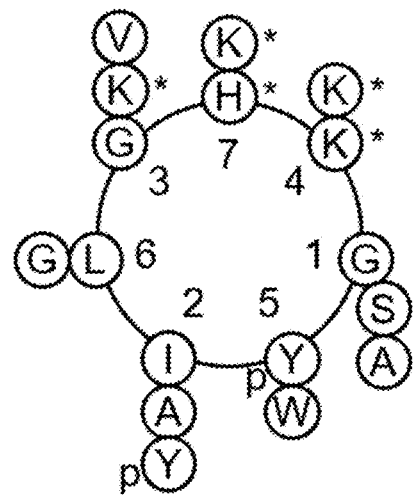
Figure 3C:
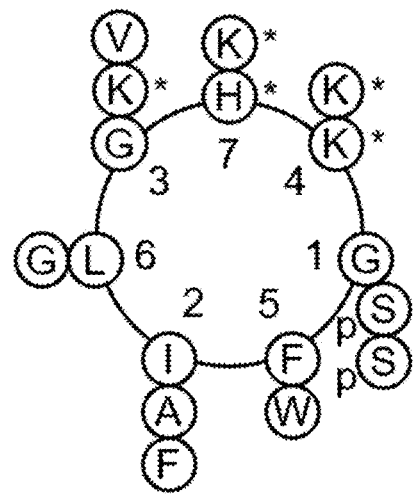
Figure 3D:
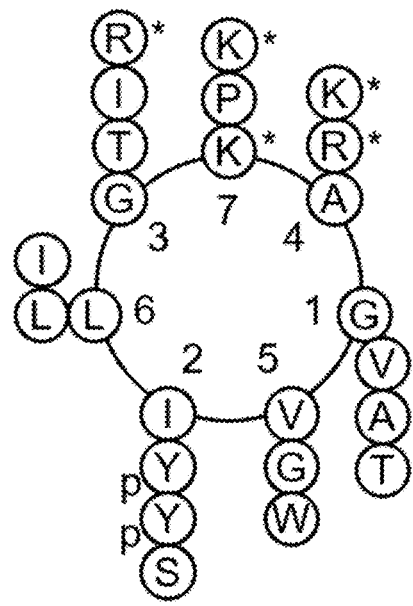
Figure 3E:
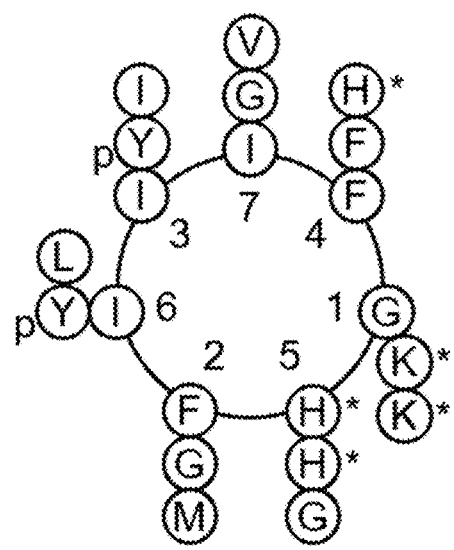

Another exemplified membrane lytic motif is EP1 (SEQ ID NO: 7), and the helical wheel diagram of which is depicted in FIG. 2G. There are 3 corresponding sites in EP1, they are the corresponding sites 1, 4, and 5, which are adjacent to each other, and respectively comprise 2, 1, and 2 positive-charged amino acid residue(s). In the case when EP1 is employed as the membrane lytic motif of the present synthetic polypeptide, the masking motif is linked to the C-terminus of the valine (V) residue at the corresponding site 7 of the membrane lytic motif via the linker.

According to certain embodiments of the present disclosure, the masking motif of the present synthetic polypeptide is a peptide, which comprises at least 10 (e.g., 10, 11, 12, 13, 14, 15, 16, 17, 18, 19, 20, or more) negative-charged amino acid residues to disrupt the secondary structure of the membrane lytic motif. Preferably, the masking motif comprises at least 10 glutamate residues. In one specific example of the present disclosure, the masking motif consists of 12 glutamate residues.

The linker for linking the membrane lytic motif and the masking motif of the present synthetic polypeptide is a stimuli-responsive linker, for example, a photocleavable or protease-cleavable moiety. According to some embodiments, the linker of the present disclosure is a photocleavable moiety, for example, a moiety derived from unnatural amino acid 3-amino-3-(2-nitrophenyl)propionic acid (ANP), or 4-(4-(1-aminoethyl)-2-methoxy-5-nitrophenoxy)butanoic acid. In one specific embodiment, the photocleavable moiety has the structure of formula (I) or formula (II):

(I)

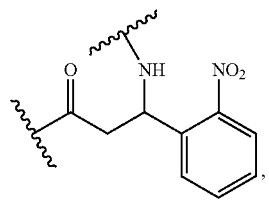

(II)

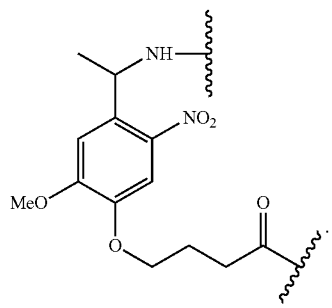

According to alternative embodiments, the linker of the present disclosure is a protease-cleavable moiety, for example, a moiety cleavable by matrix metalloproteinase (MMP), or cathepsin. In some specific examples, the linker comprises the amino acid sequence of SEQ ID NO: 23 or 24. In one specific example, the linker is a valine-citrulline dipeptide.

Alternatively, the masking motif of the present synthetic polypeptide may be a phosphoryl ($PO_3^{2-}$) group, which is linked to the alcohol sidechain of the phosphorylatable amino acid residue (e.g., the sidechain of the serine (S), tyrosine (Y), and/or threonine (T) residues) of the membrane lytic motif via a phosphatase-cleavable linker (such as, a phosphoester bond) thereby forming a phosphorylated amino acid residue. In the alternative embodiments, the number of the phosphorylated S, Y and/or T residues in the present synthetic polypeptide is at least 2 (e.g., 2, 3, 4, 5, 6, 7, or more). When the membrane lytic motif is aligned into the alpha-helical structure, the corresponding site comprising the S, Y and/or T residue(s) having the masking motif (i.e., the phosphoryl group) linked thereto is different from the corresponding site comprising one or more of the positive-charged amino acid residues. In other words, the phosphorylated S, Y and/or T residue(s), and the K, R and/or H residue(s) would not be present in the same corresponding site.

Reference is now made to FIG. 3A, in which the alpha-helical structure of Magainin 2-3pY (SEQ ID NO: 8) is projected on a helical wheel diagram. The positive-charged amino acid residues (i.e., the K, R, and/or H residues) are marked by symbol "*", and the amino acid residues having the phosphoryl group linked thereto (i.e., the phosphorylated amino acid residues) are marked by symbol "p" in FIG. 3A. According to FIG. 3A, the number of the phosphorylated amino acid residues is 3, i.e., three Y residues respectively disposed at the corresponding sites 2 and 5, which are different from the corresponding sites comprising the positive-charged amino acid residues, i.e., the corresponding sites 3, 4, and 7.

FIG. 3B provides an alternative example of the present synthetic polypeptide that depicts the helical wheel diagram of Magainin 2-2pY (SEQ ID NO: 9). As depicted in FIG. 3B, Magainin 2-2pY comprises two phosphorylated Y residues respectively at the corresponding sites 2 and 5, and five positive-charged amino acid residues respectively at the corresponding sites 3, 4, and 7.

Another exemplified synthetic polypeptide is Magainin 2-2pS (SEQ ID NO: 10). The Magainin 2-2pS comprises two phosphorylated S residues in the amino acid sequence. As depicted in FIG. 3C, the two phosphorylated S residues are disposed at the corresponding site 1, while five positive-charged amino acid residues (i.e., one H residue, and four K residues as marked in FIG. 3C) are respectively disposed at the corresponding site 3, 4, and 7.

Another exemplified synthetic polypeptide is Melittin mutation-2pY (SEQ ID NO: 11). As depicted in FIG. 3D, the corresponding site 2 comprises two phosphorylated Y residues, while the adjacent corresponding sites 3, 4, and 7 respectively comprise 1, 2, and 2 positive-charged amino acid residues.

An alternative example of the present synthetic polypeptide is provided in FIG. 3E that depicts the helical wheel diagram of EP1-2pY (SEQ ID NO: 12). In the helical alignment of EP1-2pY, there are two phosphorylated Y residues at the corresponding sites 3 and 6, and five positive-charged amino acid residues at the corresponding sites 1, 4, and 5.

In addition to the alpha-helical structure and helical wheel diagram as described above, the present synthetic polypeptide may alternatively be represented by the formula of $(X_1)_{1-4}(X_2)_{1-13}(X_1)_{1-4}$, in which each $X_1$ is independently selected from the group consisting of, lysine, arginine, and histidine residues, and each $X_2$ is independently selected from the group consisting of serine, threonine, asparagine, glutamine, cysteine, glycine, proline, alanine, valine, isoleucine, leucine, methionine, phenylalanine, tyrosine, tryptophan, aspartate, and glutamate residues. Preferably, each $X_2$ is independently selected from the group consisting of serine, threonine, asparagine, glutamine, cysteine, glycine, proline, alanine, valine, isoleucine, leucine, methionine, phenylalanine, tyrosine, and tryptophan residues. Further, in the case when the present synthetic polypeptide comprises two or more $X_1$, and one or more $X_2$ amino acid residues, then each $X_1$ in the first and second stretches of $(X_1)_{1-4}$ of the formula $(X_1)_{1-4}$ $(X_2)_{1-13}(X_1)_{1-4}$ may be same or different amino acid residues; similarly, each $X_2$ in the stretch $(X_2)_{1-13}$ of the formula $(X_1)_{1-4}$ $(X_2)_{1-13}$ $(X_1)_{1-4}$ may be same or different amino acid residues.

In the case when the membrane lytic motif is Magainin 2 (SEQ ID NO: 1), $X_1$ in the first and second stretches of $(X_1)_{1-4}$ of formula $(X_1)_{1-4}(X_2)_{1-13}(X_1)_{1-4}$ is K and H, respectively; while $(X_2)_{1-13}$ of formula $(X_1)_{1-4}(X_2)_{1-13}(X_1)_{1-4}$ has the amino acid sequence of "FL". As to Melittin (SEQ ID NO: 4), $X_1$ in the first stretch of $(X_1)_{1-4}$ of formula $(X_1)_{1-4}$ $(X_2)_{1-13}(X_1)_{1-4}$ is K, $(X_2)_{1-13}$ of formula $(X_1)_{1-4}(X_2)_{1-13}$ $(X_1)_{1-4}$ has the amino acid sequence "VLTTGLPALISWI"

(SEQ ID NO: 25), and the second stretch of $(X_1)_{1-4}$ of formula $(X_1)_{1-4}(X_2)_{1-13}(X_1)_{1-4}$ has the amino acid sequence "KRKR" (SEQ ID NO: 26).

According to certain working examples of the present disclosure, the membrane lytic motif comprises any of the amino acid sequences of SEQ ID NOs: 1-12.

The synthetic polypeptide in accordance with any embodiment of the present disclosure is useful in the preparation of a stimuli-responsive liposome, which may release the agent (e.g., the therapeutic agent, or the contrast agent) encapsulated therein upon exposure to a stimulus, for example, light or enzyme (e.g., MMP or phosphatase). Specifically, upon coupling to the lipid layer of a liposome, the present synthetic polypeptide remains inactive until it is exposed to a stimulus that cleaves away the linker that results in the separation of the masking motif from the membrane lytic motif, which in turn exerts membrane lytic activity on the liposome that leads to the disruption of the intact structure of the liposome, and releases the agent encapsulated in the liposome to the target site.

According to some embodiments of the present disclosure, the liposome comprises a center core for encapsulating a therapeutic agent or a reporter molecule; a lipid layer encapsulating the center core; and a synthetic polypeptide coupled to the lipid layer; in which the synthetic polypeptide is any polypeptide of the present disclosure.

The method for preparing liposomes is well-known in the technical fields of the present invention. Suitable methods for preparing the present liposome include, but are not limited to, extrusion, reverse phase evaporation, ultrasonic, solvent (e.g., ethanol) injection, microfluidization, detergent dialysis, ether injection, dehydration/rehydration, and a combination thereof.

For the purpose of incorporating the polypeptide to the liposome, peptide can be bioconjugated to liposomal lipid before or after liposome formation so as to produce the final peptidyl liposome, in which the component (e.g., the lipid) contains less than 1% of peptidyl lipid. This can be done by mixing trace amount of peptidyl lipid (less than 1% of total lipid) to generate peptide-conjugated lipid film before liposome formation; or, alternatively, by mixing trace amount of reactive lipids (less than 1%) to form surface-reactive liposome for later peptide bioconjugation. To crosslink between peptide and lipid, no matter before or after liposome formed, the polypeptide and lipid can be coupled via forming an amide bond, thioether bond, or click chemistry. The component (e.g., the lipid) of the liposome may be modified by amine reactive group, such as N-hydroxysuccinimide esters (NETS), a succinyl group, a cyano group, a glutaryl group, or carboxylic acid. Or alternatively, a sulfhydryl reactive group, such as a maleimide group, alkyl bromide/iodide, iodoacetamide, or pyridyldithiopropionate (PDP). Accordingly, the polypeptide can be coupled to the liposome via forming a thiol-maleimide reaction occurred between the thiol group of the polypeptide and the sulfhydryl reactive group of the liposome. As would be appreciated, the liposome may alternatively be modified by other groups, e.g., a carboxylic acid reactive group, an azide reactive group, or a dibenzocyclooctyne (DBCO) reactive group, so that the polypeptide having a corresponding group can be coupled to the liposome via a suitable reaction. According to one embodiment of the present disclosure, the present polypeptide is coupled to the liposome via a thiol-maleimide reaction, in which the present polypeptide is modified by adding a cysteine residue at the N-terminus thereof so that it can be coupled to the maleimido lipid of the liposome.

The therapeutic agent may vary with desired purposes. For example, the therapeutic agent may be an anti-tumor agent, an anti-inflammatory agent, an anti-microbial agent, an anti-oxidant agent, a growth factor, a neuron transmitter, or a protein inhibitor.

Exemplary anti-tumor agents include, but are not limited to, curcumin, interferons, cytokines (e.g., tumor necrosis factor, interferon α, interferon γ), antibodies (e.g. Herceptin (trastuzumab), T-DM1, AVASTIN (bevacizumab), ERBITUX (cetuximab), Vectibix (panitumumab), Rituxan (rituximab), and Bexxar (tositumomab)), anti-estrogens (e.g. tamoxifen, raloxifene, and megestrol), LHRH agonists (e.g. goscrelin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), *vinca* alkaloids (e.g. vincristine, vinblastine, vindesine, and vinorelbine), taxoids (e.g. paclitaxel or a paclitaxel equivalent such as nanoparticle albumin-bound paclitaxel (Abraxane), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin A analogs, Vitamin D3 analogs (e.g. EB 1089, CB 1093, and KH 1060), vitamin K, isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin (DOX), pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine. According to some working examples of the present disclosure, the therapeutic agent is doxorubicin (DOX).

Examples of anti-inflammatory agent include, but are not limited to curcumin, non-steroidal anti-inflammatory drugs (NASIDs) including, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

The anti-microbial agent may be an anti-bacterial agent, an anti-viral agent, an anti-fungal agent, or an anti-parasite agent.

Non-limiting examples of anti-oxidant agents include amine (e.g., N,N-diethylhydroxylamine, and amino-guanidine), arginine pilolate, ascorbic acid and its salts, ascorbyl ester of fatty acid, bioflavonoid, butylated hydroxy benzoic acid and its salt, dihydroxy fumaric acid and its salts, gallic acid and its alkyl esters (e.g., propyl gallate, and uric acid), glycine pidolate, 6-hydroxy-2,5,7,8-tetramethylchroman-2-carboxylic acid, lipoic acid, lysine, melanin, methionine, nordihydroguaiaretic acid, proline, silymarin, sorbic acid and its salts, sulfhydryl compounds (e.g., glutathione), superoxide dismutase, catalase, tea extract, grape skin/seed extract, rosemary extract, tocopherol acetate, tocopherol, tocopherol sorbate, and a combination thereof.

Non-limiting examples of the growth factor include, but are not limited to, angiopoietin, macrophage colony-stimulating factor (M-CSF), granulocyte colony-stimulating factor (G-CSF), granulocyte macrophage colony-stimulating factor (GM-CSF), placental growth factor (PLGF), vascular endothelial growth factor (VEGF), fibroblast growth factor (FGF), epidermal growth factor (EGF), one morphogenetic protein (BMP), endoglin, endothelin, leptin, follistatin, hepatocyte growth factor (HGF), insulin-like growth factor (IGF), keratinocyte growth factor (KGF), nerve growth factor (NGF), growth factor-α (TGF-α), transforming growth factor-β (TGF-β), cartilage growth factor (CGF), stem cell factor (SCF), brain-derived neurotrophic factor (BDNF), platelet-derived growth factor (PDGF), interleukin (IL) and ephrin.

Examples of neuron transmitter include, but are not limited to, glutamate, aspartate, D-serine, γ-aminobutyric acid (GABA), glycine, nitric oxide (NO), carbon monoxide (CO), hydrogen sulfide ($H_2S$), dopamine (DA), norepinephrine (also known as noradrenaline), epinephrine (also known as adrenaline), histamine, serotonin (SER, 5-HT), phenethylamine, N-methylphenethylamine, tyramine, 3-iodothyronamine, octopamine, tryptamine, oxytocin, somatostatin, substance P, acetylcholine (ACh), anandamide, and a combination thereof.

Additionally or alternatively, the center core may comprise a reporter molecule, such as, a contrast agent or a fluorescent molecule. The contrast agent may be any substance useful in improving the contrast of the structure or fluid within the body in medical imaging. Non-limiting examples of the contrast agent include, paramagnetic contrast agent, superparamagnetic contrast agent, and proton density contrast agent.

More specifically, the contrast agent may be a gadolinium-based contrast agent (GBCA), polymeric (dendrameric) gadolinium complex, manganese-based MRI contrast agent, or superparamagnetic iron oxide (SPIO). Examples of GBCA include, but are not limited to, gadoteric acid and its salt (e.g., meglumine salt; such as Gd-DOTA), gadopentetic acid and its salt (e.g., dimeglumine salt; such as Gd-DTPA), gadodiamide (such as GdGd-DTPA-BMA), gadobenic acid and its salt (e.g., dimeglumine salt; such as Gd-BOPTA), gadoxetic acid and its salt (e.g., disodium salt; such as Gd-EOB-DTPA), gadoteridol (such as Gd-HP-DO3A), gadoversetamide (such as Gd-DTPA-BMEA), gadobutrol (such as Gd-DO3A-butrol), gadofosveset and its salt (e.g., trisodium salt; such as MS-325), and gadocoletic acid and its salt (e.g., trisodium salt; such as B22956/1). Examples of polymeric (dendrameric) gadolinium complex include, but are not limited to, gadomelitol (such as P792), gadodenterate (such as SH L 643 A), and gadomer 17. The manganese-based MRI contrast agent may be mangafodipir and its salt (e.g., trisodium salt; such as Mn-DPDP), Mn-DTPA-SA, Mn-EDTA, or Mn-porphyrin derivatives (including, TPP, TPPS2, TPPS3, TPPS4, mesoporphyrin, hematoporphyrin, uroporphyrin, ATN-10, HOP-8P etc.). Regarding SPIO, it may be ferumoxytol, ferucarbotran, or ferumoxide. According to one specific example of the present disclosure, the reporter molecule is diethylenetriaminepentaacetic acid gadolinium (III) ($Gd^{3+}$-DTPA).

Regarding the fluorescent molecule, it may be any molecule that may re-emit light upon light excitation, for example, cyanine (including Cy2, Cy3, Cy3B, Cy3.5, Cy5, Cy5.5 and Cy7), green fluorescent protein (GFP), enhanced green fluorescent protein (eGFP), red fluorescent protein (RFP), yellow fluorescent protein (YFP), fluorescein isothiocyanate (FITC), phycoerythrin (PE), or allophycocyanine (APC). According to one working example, the fluorescent molecule is Cy5.5.

Also disclosed herein are methods for diagnosing or treating a disease in a subject by use of the liposome of the present disclosure. The method for diagnosing a disease comprises administering to the subject an effective amount of the present liposome, which comprises a reporter molecule (e.g., Gd'-DTPA) in the center core. For the purposes of treating a disease in a subject, an effective amount of the present liposome, which comprises a therapeutic agent (e.g., DOX) in the center core, is administered to the subject so as to ameliorate or alleviate the symptoms associated with the disease.

The disease treatable with the present liposome and/or method may be a tumor, an inflammatory disease, an infectious disease, a disease or condition associated with oxidative stress or abnormal expression of growth factor, or a neurological disease.

The subject is a mammal, e.g., a human, mouse, rat, guinea pig, monkey, chimpanzee, rabbit, pig, cat, dog, horse, cow, sheep, or goat. Preferably, the subject is a human.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods
Agents
The phospholipids, 1,2-di stearoyl-sn-glycero-3-phosphoethanolamine-N-[methoxy(polyethylene glycol)-2000] (DSPE-PEG2000), 1,2-dipalmitoyl-sn-glycero-3-phosphoethanolamine-N-[4-(p-maleimidomethyl)cyclohexane-carboxamide] (16:0 PE MCC), 1,2-dioleoyl-sn-glycero-3-phosphoethanolamine-N-[4-(p-maleimidomethyl)cyclohexane-carboxamide] (18:1 PE MCC), L-α-phosphatidylcholine, hydrogenated (Soy) (HSPC), and 1,2-distearoyl-sn-glycero-3-phosphocholine (DSPC) were purchased from Avanti Polar Lipids, Inc. Cholesterol, tricine, and sodium bicarbonate were obtained from Sigma.

Doxorubicin-HCl was obtained from Toronto Research Chemicals. Fmoc-amino acids and 2-(6-chloro-1H-benzotriazole-1-yl)-1,1,3,3-tetramethylaminium hexafluorophosphate (HCTU) were procured from Anaspec. 4-{4-[1-(9-fluorenylmethyloxycarbonyl)ethyl]-2-methoxy-5-nitrophenoxy}butanoic acid (Fmoc-photolinker) and 1-[bis(dimethylamino)methylene]-1H-1,2,3-triazolo[4,5-b]pyridinium 3-oxid hexafluorophosphate (HATU) were obtained from Advanced chemtech. N,N-diisopropylethylamine (DIPEA), trifluoroacetic acid (TFA) and triisopropylsilane (TIPS) were purchased from Alfa aesar. Dithiothreitol (DTT) was obtained from Uniregion biotech. Fetal bovine serum (FBS) was purchased from Biological Industries and was heated inactivation at 56° C. for 30 minutes. Tris(2-carboxyethyl)phosphine hydrochloride (TCEP) was purchased from Acros Organics. Dulbecco's modified Eagle's medium (DMEM), Minimum essential medium (MEM), and 3-[4,5-dimethylthiazol-2-yl]-2,5-diphenyltetrazolium bromide (MTT) were purchased from Gibco and Merck, respectively. Annexin V-Cy5 apoptosis kit was purchased from BioVision. All other chemicals used in this study were of analytical reagent grade. In this work, the human carcinoma KB cells were used to evaluate the effect of the liposome constructs.

Synthesis and Characterization of Peptides

The present polypeptides were synthesized by an automated peptide synthesizer using standard Fmoc solid-phase peptide synthesis protocol on resin with coupling agents 1-[bis(dimethylamino)methylene]-1H-1,2,3-triazolo[4,5-b]pyridinium3-oxidhexafluoro phosphate (HATU) for the coupling of proline, and 2-(6-chloro-1H-benzotriazole-1-yl)-1,1,3,3-tetramethylaminiumhexafluoro-phosphate (HCTU) for the coupling of the rest of amino acids. N,N-diisopropylethylamine (DIPEA) was used as a base. For peptide cleavage, the resins were treated with a solution of TFA/TIPS/$H_2O$ (95:2.5:2.5, v/v/v) for 90 minutes to afford crude peptides, which were precipitated by cold ether and then purified by high performance liquid chromatography (HPLC). The peptide solutions before and after photolysis were characterized by analytical reversed phase HPLC (RP-HPLC) and electrospray ionization-mass spectrometry (ESI-MS).

The synthesized peptides and the amino acid sequences thereof were summarized in Table 1.

TABLE 1

Synthesized peptides

| Peptide | Sequence | SEQ ID NO |
|---|---|---|
| Magainin 2 (full length) | GIGKFLHSAKKFGKAFVGEIMNS | 1 |
| Magainin 2 | GIGKFLHSAKKFGKAFV | 2 |
| Magainin 2 (W12) | GIGKFLHSAKKWGKAFV | 3 |

TABLE 1-continued

Synthesized peptides

| Peptide | Sequence | SEQ ID NO |
|---|---|---|
| Melittin | GIGAVLKVLTTGLPALISWIKRKRQQ | 4 |
| Melittin (mutation) | GIGAVLKVLTRGLPALIKWIKTSR | 5 |
| Pexiganan | GIGKFLKKAKKFGKAFVKILK | 6 |
| EP1 | GFIFHIIKGLFHAGKMIHGLV | 7 |
| Magainin 2-3pY | GIGK<u>Y</u>LHSAKK<u>Y</u>GKA<u>Y</u>V (Y is phosphorylated) | 8 |
| Magainin 2-2pY | GIGK<u>Y</u>LHSAKKWGKA<u>Y</u>V (Y is phosphorylated) | 9 |
| Magainin 2-2pS | GIGKFLH<u>S</u>AKKWGK<u>S</u>FV (S is phosphorylated) | 10 |
| Melittin (mutation)-2pY | GIGAVLKV<u>Y</u>TRGLPA<u>Y</u>IKWIKTSR (Y is phosphorylated) | 11 |
| EP1-2pY | GFIFHIIKG<u>Y</u>FH<u>Y</u>GKMIHGLV (Y is phosphorylated) | 12 |
| Magainin 2-pY | *GIGKFLHSAKK<u>Y</u>GKAFV* (Y is phosphorylated) | 13 |
| Magainin 2-pS | *GIGKFLH<u>S</u>AKKWGKAFV* (S is phosphorylated) | 14 |
| Scrambled Magainin 2 | *KFWHAKGGGSFIAKVKL* | 15 |
| Temporin L | *FVQWFSKFLGRIL* | 16 |
| TP4 | *GFIHHIIGGLFSAGKAIHRLIRRRRR* | 17 |
| LL37 | *LLGDFFRKSKEKIGKEFKRIVQRIKDFLRNLVPRTES* | 18 |
| Buforin II | *TRSSRAGLQFPVGRVHRLLRK* | 19 |
| Ranalexin | *FLGGLIKIVPAMICAVTKKC* | 20 |
| Bactenecin 1 | *RLCRIVVIRVCR* | 21 |
| Thanatin | *GSKKPVPIIYCNRRTGKCQRM* | 22 |
| Linker-1 | SPAYYTAA | 23 |
| Linker-2 | PLGVRG | 24 |

*The amino acid sequences in italic serve as negative controls in the experiment.

Preparation of Liposomes and Peptidyl Liposomes

Liposomal DOX (i.e., the liposome having doxorubicin encapsulated therein) was prepared using a reported method. In brief, lipid composition of HSPC or DSPC, cholesterol, DSPE-PEG2000, and maleimido lipid at the molar ratio ranging from 38-60%, 40-55%, 0-5%, and 0.1-2% were used for general preparation. Lipid ingredients (12 mg) were dissolved in chloroform in a round bottom flask and then evaporated using a rotary evaporator to form a lipid film, rehydrated by trapping agent buffer (ammonium sulfate), and then subjected to freeze-thaw cycles. Lipid suspension was gently agitated and subsequently extruded through polycarbonate membranes (0.1 μm pore size) using a mini extruder to obtain uniform size liposome. The cross membrane ammonium sulfate gradient of liposome was generated by size exclusion chromatography of liposome using 150 mM NaCl solution as an eluent. DOX (5 mM, 50 μl) was added into the collected ammonium sulfate-entrapped liposomes (5 mM, 500 μl) and incubated for 45 minutes at 60° C. to actively load DOX into liposome. A subsequent gel filtration equilibrated in tricine buffer (50 mM Tricine, 100 mM NaCl, pH 7.4) was used to purify DOX-encapsulated liposomes from the non-encapsulated DOX. The DOX-encapsulated liposome was then allowed to store at 4° C. The loading efficiency of DOX was estimated to be 95%.

For peptide-maleimido liposome conjugation, cysteinyl-peptides were reduced in tricine buffer (50 mM Tricine, 100 mM NaCl, pH 7.4) and then added into DOX-encapsulated liposome solution at a desired molar ratio (peptide/lipid ratio ranging from 1/1200 to 1/300). They were gently shaken, followed by the addition of DTT (1 mM) to quench the unreacted maleimido group presented on the liposomal surface at 37° C. for 30 minutes. All liposomes of the present disclosure were purified by size exclusion chromatography. The thus-produced peptidyl liposomes comprising DOX as the therapeutic agent were summarized in Table 2.

TABLE 2

Peptidyl liposomes of the present disclosure

| No.<br>(Liposome name) | Synthetic polypeptide coupled<br>to the liposome (Polypeptide name) |
|---|---|
| *Photo-responsive liposome* | |
| 1<br>(1-MDL) | Magainin 2 (W12) (SEQ ID NO: 3) - photolinker*- 12 E residues<br>(peptide 1) |
| 2 | Melittin (SEQ ID NO: 4) - photolinker*- 12 E residues |
| 3 | Melittin (mutation) (SEQ ID NO: 5) - photolinker*- 12 E residues |
| 4 | Pexiganan (SEQ ID NO: 6) - photolinker*- 12 E residues |
| 5 | EP1 (SEQ ID NO: 7) - photolinker*- 12 E residues |
| 6<br>(2-MDL) | Scramble Magainin 2 (SEQ ID NO: 15) - photolinker*-12 E residues<br>(peptide 2) |
| 7 | TP4 (SEQ ID NO: 17) - photolinker*-12 E residues |
| 8 | Temporin L (SEQ ID NO: 16) - photolinker*-12 E residues |
| *Phosphatase-responsive liposome* | |
| 9 | Magainin 2-3pY (SEQ ID NO: 8) |
| 10<br>(3-MDL) | Magainin 2-2pY (SEQ ID NO: 9)<br>(peptide 3) |
| 11<br>(4-MDL) | Magainin 2-2pS (SEQ ID NO: 10)<br>(peptide 4) |
| 12 | Melittin (mutation)-2pY (SEQ ID NO: 11) |
| 13 | EP1-2pY (SEQ ID NO: 12) |
| 14 | Magainin 2-pY (SEQ ID NO: 13) |
| 15 | Magainin 2-pS (SEQ ID NO: 14) |
| *MMP2-responsive liposome* | |
| 16<br>(5-MDL) | Magainin 2 (W12) (SEQ ID NO: 3) - linker (SEQ ID NO: 23) - 12 E residues<br>(peptide 5) |
| 17<br>(6-MDL) | Magainin 2 (W12) (SEQ ID NO: 3) - linker (SEQ ID NO: 24) - 12 E residues<br>(peptide 6) |
| 18 | EP1 (SEQ ID NO: 7) - linker (SEQ ID NO: 24) - 12 E residues |
| 19 | TP4 (SEQ ID NO: 17) - linker (SEQ ID NO: 24) - 12 E residues |

*Photolinker 4-(4-(1-aminoethyl)-2-methoxy-5-nitrophenoxy)butanoic acid

Drug-Releasing Analysis

DOX release can be quantified by the Dox release-induced fluorescence to evaluate the drug-releasing (using DOX as encapsulated model drug) properties of the present peptidyl liposomes, the fluorescence of photo-responsive liposomes were measured by incubated in the presence or absence of UV irradiation (5 mW/cm$^2$, 10 minutes) at 37° C. for 1 hour. The fluorescence of phosphatase-responsive liposomes were measured by incubating the liposomes in the presence or absence of ALP (50 U/ml) at 37° C. for 3 hours. The fluorescence of MMP2-responsive liposomes were measured by incubating the liposomes in the presence or absence of MMP2 (300 ng/ml) at 37° C. for 1 hours. The drug-releasing percentage was calculated by equation (1) and data was summarized in Table 3.

Characterization of Liposomes

Phospholipid concentration quantification was performed based on the reported protocol. In brief, 8.9 N of $H_2SO_4$ (0.45 ml) was added into liposome (15 and 30 μl) and standard solutions ($NaH_2PO_4$, 32.5 to 227.5 nmole) separately, and were heated above 200° C. for 25 minutes. After cooling, 10% $H_2O_2$ (0.15 ml) was added to sample and standard solutions and reheated above 200° C. for 30 minutes. After cooling, a mixture of $H_2O$ (3.9 ml), ammonium molybdate tetrahydrate (2.5% w/v, 0.5 ml), and ascorbic acid (10% w/v, 0.5 ml) was added sequentially and reheated at 100° C. for 7 minutes. The concentration of phospholipid in the liposome sample was calculated using calibration curve of standard solutions at $OD_{820}$. For a typical liposome particle size or zeta-potential measurement, 100 μl of liposome solution was diluted in 1 ml of tricine buffer (50 mM Tricine, 100 mM NaCl, pH 7.4) and was placed into a microcuvette or zeta-potential cuvette for triplicated measurements per sample.

Liposomal DOX Release Estimated by Fluorescence

The fluorescence intensity of trigger-release liposomal DOX (I) was measured in the presence or absence of UV irradiation (5 mW/cm$^2$, 0-60 minute) after incubation at 37° C. for 1 hour. The fluorescence intensity of complete liposomal DOX release ($I_{max}$) was achieved by the addition of 1% Triton™ X-100 and incubated at 70° C. for 2 minutes. The percentage of content release caused by the peptides photoactivation was calculated by equation (1):

$$\text{Trigger-induced Release (\%)} = [(I-I_o)/(I_{max}-I_o)] \times 100\% \quad (1)$$

where $I_o$ is the initial fluorescence intensity of the liposomes before trigger activation.

Liposomal DOX Release Estimated by Cryo-Electron Microscopy (Cryo-EM)

Liposome solutions treated with UV irradiation (5 mW/cm$^2$, 10 min) or dark condition were incubated at 37° C. for 1 hour to complete DOX release. The photography for cryo-EM images of liposomes was acquired by cryo-TEM. Briefly, 400-mesh copper grids were glow-discharged in an (Ar, $O_2$)-atmosphere for 10 seconds on carbon side. 4 μl of liposome solution (0.2-0.4 mg/ml of total lipid) was pipetted onto the surface of the grids. Grids were blotted in 100% humidity at 4° C. for 3-4 seconds and plunged into liquid ethane bath cooled by liquid nitrogen. The release percentage of DOX from light-triggered liposome was calculated using the following equation (2):

$$\text{Trigger-induced Release} = (EL_{Liposome} - EL_{DDL\text{-}dark})/(100\% - EL_{DDL\text{-}dark}) \quad (2)$$

where EL is the percentage of counted empty liposome in cryo-EM picture.

Cellular DOX Uptake of Free DOX and Peptidyl Liposomes

For the fluorescence microscope image of cellular uptake of DOX, KB cells ($5\times10^5$ cells per well) were seeded on 35 mm μ-dish in DMEM with 10% FBS at 37° C. for 24 hours. Then, the medium was replaced by the MEM medium (without FBS) containing free DOX, or the MEM medium (without FBS) containing DDL, 1-MDL or 2-MDL, in the presence or absence of light irradiation (5 mW/cm$^2$, 10 minutes), and incubated at 37° C. for additional 20 hours. Cells were then washed and kept in MEM containing 10% FBS during observation under a fluorescence microscope. Cells were stained with Hoechst 33342 at 37° C. for 20 minutes to visualize nuclei. The Hoechst and DOX fluorescence were visualized using preset filter cubes.

For the time-dependent cellular DOX uptake, KB cells ($3\times10^4$ cells per well) were seeded on an 8 well μ-slide in DMEM with 10% FBS at 37° C. for 24 hours. Then, the medium was replaced by the MEM medium (without FBS) containing free DOX, or the MEM medium (without FBS) containing DDL or 1-MDL, in the presence or absence of light irradiation (5 mW/cm$^2$, 4 minutes). The fluorescence images were acquired every 15 minutes with a 40× objective lens by confocal microscopy.

To correlate photo-induced liposomal DOX release and cell apoptosis by flow cytometer, KB cells ($2\times10^5$ cells per well) were seeded on a 12 well plate in DMEM with 10% FBS at 37° C. for 24 hours. Then, the medium was replaced by the MEM medium (without FBS) containing free DOX, or the MEM medium (without FBS) containing DDL or 1-MDL, in the presence or absence of light irradiation (5 mW/cm$^2$, 4 minutes), and then incubated at 37° C. for additional 20 hours. Cells were washed by 1 ml PBS and trypsinized by 1 ml trypsin-EDTA for 3 minutes, and collected by 1000 rpm centrifugation. The cell pellet was resuspended in 500 μl of PBS with 1% FBS. 7 μl of Annexin V-Cy5 was added and incubated for 5 minutes in dark. Cells in each samples (10,000 counts) were analyzed by flow cytometry.

To correlate photo-induced liposomal DOX release and cell apoptosis by high content imaging, KB cells ($1\times10^4$ cells per well) were seeded on a 96 well plate in DMEM with 10% FBS at 37° C. for 24 hours. Then, the medium was replaced by the MEM medium (without FBS) containing free DOX, or the MEM medium (without FBS) containing DDL or 1-MDL, in the presence or absence of light irradiation (5 mW/cm$^2$, 4 minutes), and then incubated at 37° C. for additional 20 hours. Cells were then washed and kept in MEM containing 10% FBS. Cells were stained with Hoechst 33342 and Annexin V-Cy5 at 37° C. for 20 and 5 minutes, respectively, to visualize nuclei and apoptotic cells. Cells (>2,000 counts) in each well were imaged by confocal quantitative image cytometer.

MTT Assay

For the half maximal inhibitory concentration (IC$_{50}$) measurement of each liposomal DOX, KB cells ($1.1\times10^4$ cells per well) were seeded on a 96 well plate in DMEM with 10% FBS at 37° C. for 24 hours. Then, the medium was replaced by the MEM medium (without FBS) containing free DOX, or the MEM medium (without FBS) containing DDL or MDL, in the presence or absence of light irradiation (5 mW/cm$^2$, 4 minutes), and then incubated at 37° C. for additional 20 hours. The medium was further replaced to MEM with 10% FBS for another 20 hours incubation at 37° C. 20 μl of MTT stock solution (5 mg/ml in PBS) was added to each well incubated at 37° C. for 2 hours, then removed 170 μl of culture medium followed by the addition of 200 μl of DMSO to each well to dissolve the purple formazan product at 37° C. on a 120 rpm reciprocal shaker for 10 minutes. The absorbance of the formazan product in DMSO solution at 540 nm was measured by plate reader so as to estimate cellular viability.

Remote Loading of Cy5.5 into Liposome

Lipid ingredients were dissolved in chloroform in a round bottom flask and then evaporated using a rotary evaporator to form a lipid film. The film was rehydrated by trapping agent solution (100 mM of sucrose octasulfate ammonium), and then subjected to ten freeze-thaw cycles. Lipid suspension was gently agitated and subsequently extruded through polycarbonate membranes (0.1 μm pore size) using a mini extruder to obtain uniform size liposome. The transmembrane trapping agent gradient of liposome was generated by removing untrapped sucrose octasulfate ammonium by size exclusion chromatography using eluting buffer (150 mM NaCl). Cy5.5 (0.02 molar equivalence of total lipid) was added to collected liposome. A subsequent filtration by size exclusion chromatography was used to purify Cy5.5 liposomes. The encapsulated efficiency percentage of Cy5.5 liposomes were calculated using the following equation (3):

$$\text{Encapsulated efficiency (\%)} = (M_L/M_T)*100\% \quad (3);$$

where $M_L$ is the amount of Cy5.5 in the liposome fraction, and $M_T$ is the amount of total Cy5.5 before purification. The loading efficiency of Cy5.5 was calculated to be 80%.

Photo-Induced Gd$^{3+}$-DTPA Encapsulated Liposome Preparation and Release

Lipid ingredients (24 mg) were dissolved in chloroform in a round bottom flask and then evaporated using a rotary evaporator to form a lipid film. The film was rehydrated by 1 ml of 200 mM Gd$^{3+}$-DTPA at pH 7.4, and then subjected to ten freeze-thaw cycles. Lipid suspension was gently agitated and subsequently extruded through polycarbonate membranes (0.1 μm pore size) using a mini extruder or ultrasonication to obtain uniform size (about 100 nm) liposome. A subsequent filtration by size exclusion chromatography equilibrated in tricine buffer (50 mM Tricine, 100 mM NaCl, pH 7.4) was used to purify Gd$^{3+}$-DTPA encapsulated liposome. For photo-triggered release, peptide 1 (0.2 mM) were reduced in tricine buffer (50 mM Tricine, 100 mM NaCl, pH 7.4) for 15 minutes at room temperature to reduce possible inter-peptide disulfide, and then added into Gd$^{3+}$-DTPA-encapsulated liposome solution at a desired molar ratio (peptide/lipid ratio ranging from 1/900 to 1/300). They were gently shaken (120 rpm on reciprocal shaker) at 37° C. for 1 hour, followed by the addition of DTT (1 mM) to quench the unreacted maleimido group presented on the liposomal surface at 37° C. for 30 minutes. The peptide 1 was added to the Gd$^{3+}$-DTPA liposome (GL) to afford the peptide 1 conjugated Gd$^{3+}$-DTPA liposome (designated as "1-MGL"), or DTT conjugated Gd$^{3+}$-DTPA liposome (designated as "DGL"). Peptidyl liposomes were purified by size exclusion chromatography. The trigger release of liposomal Gd$^{3+}$-DTPA was measured in the presence or absence of UV irradiation (5 mW/cm$^2$, 10 minutes) after incubation at 37° C. for 1 hour. $T_1$ relaxation time of liposome solution was calculated from the images obtained with a $T_1$-weighted spin echo sequence where TR=90, 120, 150, 180, 230, 290, 330, 380, 450, 550, 680, 850, 1000, 1500, 2000, 3000, 5000, 8000 ms, with TE=8 ms, number of excitation=1, field-of-view=6.5×6.5 cm$^2$, and matrix size=256×256.

Example 1 Characterization of the Present Liposome

The drug-releasing properties of the present synthesized liposomes were analyzed in accordance with procedures described in Materials and Methods. The data was summarized in Table 3.

TABLE 3

Drug-releasing properties of the present liposome

| Liposome No. | Dox releasing % (Before stimulation) | Dox releasing % (After stimulation) |
|---|---|---|
| 1 (1-MDL) | 5% | 80% |
| 2 | 5% | 50% |
| 3 | 5% | 80% |
| 4 | 5% | 50% |
| 5 | 5% | 45% |
| 6 (2-MDL) | 5% | 15% |
| 7 | 5% | 10% |
| 8 | 5% | 15% |
| 9 | 5% | 70% |
| 10 (3-MDL) | 5% | 70% |
| 11 (4-MDL) | 5% | 45% |
| 12 | 5% | 70% |
| 13 | 5% | 35% |
| 14 | 5% | 10% |
| 15 | 5% | 10% |
| 16 (5-MDL) | 5% | 50% |
| 17 (6-MDL) | 5% | 40% |
| 18 | 5% | 25% |
| 19 | 5% | 10% |

*Stimulation: photo irradiation for liposomes Nos: 1-8; phosphatase treatment for liposomes Nos: 9-15; MMP2 treatment for liposomes Nos: 16-19.

The data of Table 3 indicated that Liposome Nos: 1-5, 9-13, 16-18 respectively showed 80%, 50%, 80%, 50%, 45%, 70%, 70%, 45%, 70%, 35%, 50%, 40%, and 25% release after stimuli triggering. These peptidyl liposomes were the successful examples of trigger-release liposomes, and the masking motif of these peptides incorporated to and/or on the liposomes were designed as illustrated in the present disclosure. Meanwhile, Liposome No: 6-8, 14-15, and 19 respectively showed 15%, 10%, 15%, 10%, 10%, and 10% release after stimuli triggering. Those peptidyl liposomes were the failed examples for trigger release. For those membrane lytic peptides not fitting the criteria of membrane lytic motif as set forth in the present disclosure, they were either too membrane active to mask, or too membrane inert to cause liposome release; accordingly, the liposomes having such the peptides conjugated would fail to achieve the trigger-release effect. Magainin 2 (W12) derivatives were the best designed membrane lytic motif to prepare trigger-release liposomes (e.g., Liposome Nos. 1, 9, 10, 11, 16, and 17) as compared to other peptides. Accordingly, Liposome Nos. 1, 6 (serving as the negative control), 10, 11, 16, and 17 were chosen for further analysis as described in Examples 2, 3, and 4, respectively.

The data of Tables 1-3 indicated that although the peptides of SEQ ID NOs: 15-22 may be conjugated with 12 E residues, however, the membrane lytic activity of these antimicrobial peptides cannot be masked or suppressed by 12 E resides. The data lead us to conclude that only peptides fulfilling the criteria of membrane lytic motif as set forth in the present disclosure can be masked by the masking motif (e.g., 12 E residues). In addition to 12 E residues, the masking effect of 4 E residues, 8 E residues, and 10 E residues were also analyzed in the experiment. The data demonstrated that only 12 E residues exhibited the capability to fully mask the membrane lytic activity, and at least 10 E residues possessed satisfying effect on masking the membrane lytic activity (data not shown). Accordingly, it is concluded that at least 10 E residues can be used as the masking motif of the present synthetic polypeptide thereby preparing the stimuli-released liposome. The data of Tables 1-3 also suggested that the drug-releasing efficacy of the peptides (e.g., the peptides of SEQ ID NOs: 13 and 14) having single one phosphoryl group conjugated thereto was obviously lower than that of the peptides (e.g., the peptides of SEQ ID NOs: 8, 9 and 10) having at least two phosphoryl groups conjugated thereto. Based on the results, it is concluded at least two phosphoryl group are required to mask the membrane lytic activity of the membrane lytic motif of the present synthesized polypeptide.

In conclusion, only the peptide fulfilling the criteria set forth in the present disclosure can be employed as the membrane lytic motif, and modified by poly-glutamate or dual (or more) phosphorylation so as to obtain the present synthesized polypeptide for preparing trigger-release liposomes.

Example 2 Characterization of Liposomes DDL, 1-MDL and 2-MDL

As summarized in Table 3, the encapsulated agent (i.e., DOX) may be efficiently released from the liposome 1-MDL upon photo-stimulation. For the purpose of further evaluating the application of 1-MDL in disease treatment, the physicochemical properties and bioactivity of 1-MDL were characterized in this example. The data were respectively illustrated in Table 4 and FIGS. 4-9.

2.1 Physicochemical Properties

In Example 2.1, the particle size, polydispersity index (PDI) and zeta-potential of the synthesized liposomes were examined, and the results were summarized in Table 4.

According to the data of Table 4, the liposomes size measured at different stages, starting from extrusion completion, DOX loading, peptide conjugation, and photoirradiation, was all approximately 130 nm in diameter as evidenced by dynamic light scattering (DLS) and cryo-EM studies. However, because of the conjugation and the consequent chemical transformation of peptides on liposomal surface, the zeta-potential of these liposomes at each stage showed a significant difference. Liposomal zeta-potential was found to be −2.2 mV after extrusion, and −2.3 mV after DOX loading (Table 4). After conjugating peptide 1 or peptide 2 with liposomes without photoirradiation, liposomal zeta-potential was negatively shifted to −6.7 and −6.2 mV but positively shifted to −2.9 and −1.7 mV after photoirradiation, respectively (Table 4). The zeta-potential of liposome decreased from −2.3 to −6.7 mV, after peptide conjugation, is possibly due to the presence of dodeca-glutamate containing peptides on liposomal surface (Table 4).

TABLE 4

Characterization of specified liposomes

| Samples | Diameter (nm) | PDI | Zeta-potential (mV) |
|---|---|---|---|
| Blank | 132 ± 36 | 0.05 ± 0.01 | −2.2 ± 0.6 |
| DL-dark | 131 ± 33 | 0.02 ± 0.02 | −2.3 ± 0.0 |
| DDL-dark | 132 ± 39 | 0.07 ± 0.03 | −2.3 ± 0.2 |
| DDL-UV | 132 ± 42 | 0.09 ± 0.02 | −2.5 ± 0.2 |
| 1-MDL-dark | 131 ± 34 | 0.04 ± 0.02 | −6.7 ± 0.8 |
| 1-MDL-UV | 131 ± 36 | 0.06 ± 0.04 | −2.9 ± 0.8 |

TABLE 4-continued

Characterization of specified liposomes

| Samples | Diameter (nm) | PDI | Zeta-potential (mV) |
|---|---|---|---|
| 2-MDL-dark | 133 ± 33 | 0.04 ± 0.00 | −6.2 ± 0.2 |
| 2-MDL-UV | 132 ± 41 | 0.09 ± 0.01 | −1.7 ± 0.4 |

Blank: the liposome without loading DOX.
DL: DOX liposome; the DOX-loaded liposome without coupling with any peptide or DTT.
DDL: DTT-DOX liposome; the DOX-loaded liposome coupling with DTT.
1-MDL: the DOX-loaded liposome coupling with peptide 1.
2-MDL: the DOX-loaded liposome coupling with peptide 2.

2.2 Drug-Releasing Efficacy Analyzed by Fluorescence

Figure 4A:
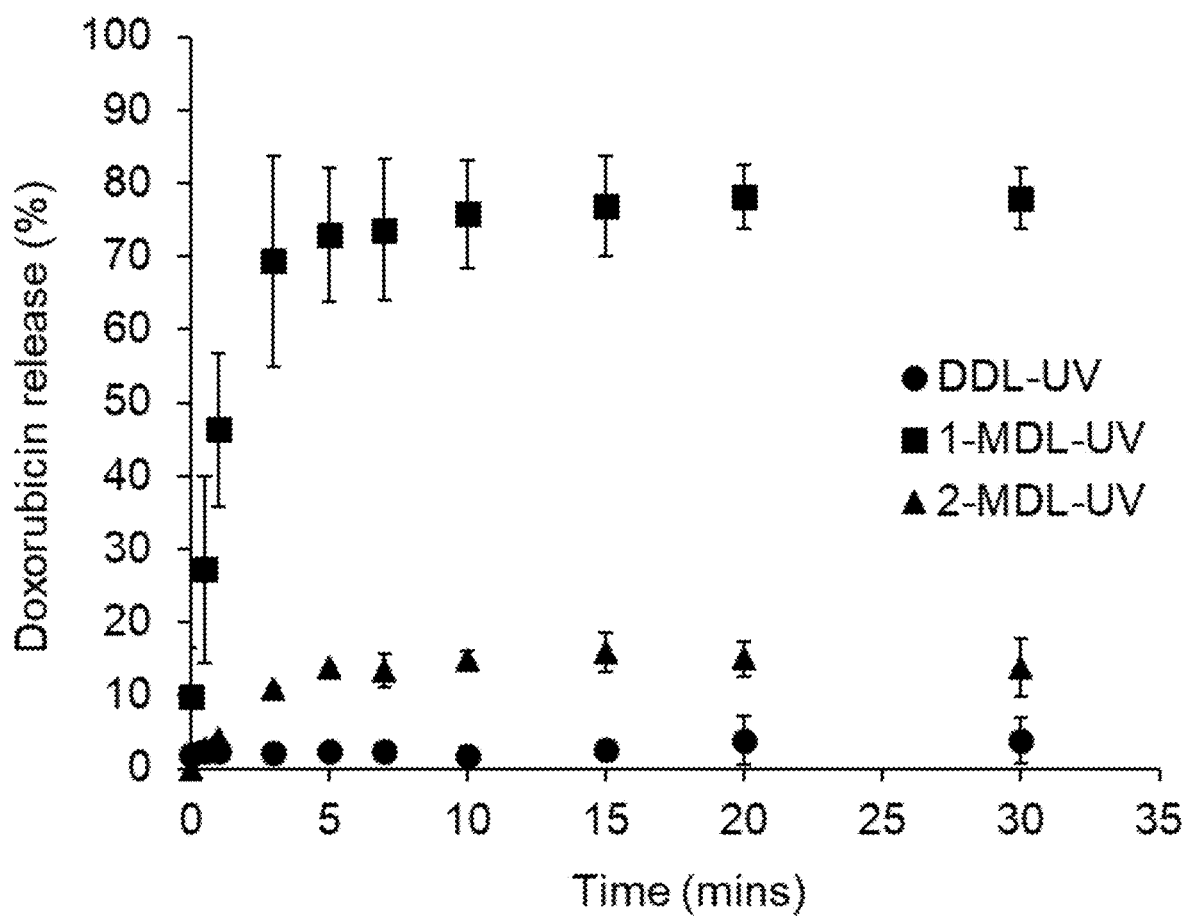
FIGS. 4A to 4D depicting release profiles of specified liposomes according to Example 2.2 of the present disclosure.

The DOX release of liposome was studied by a reported fluorescence dequenching assay. DOX release percentage of peptidyl liposomes was plotted against different irradiation time to identify the optimal irradiation duration for photoactivation as shown in FIG. 4A, indicating that 3 minutes of irradiation was sufficient to maximize the release for 1-MDL photoactivation. On the other hand, 2-MDL photoactivation only caused 15% DOX release. This result suggested that liposomal content release was triggered by the demasking of magainin 2, and the membranolytic activity of magainin 2 was highly sequence dependent, not just based on the overall peptide hydrophobicity. The DOX liposome without any peptides or DDL, showed almost no release (<5%) after irradiation, confirming that the liposome without peptide is not light-responsive.

Figure 4B:
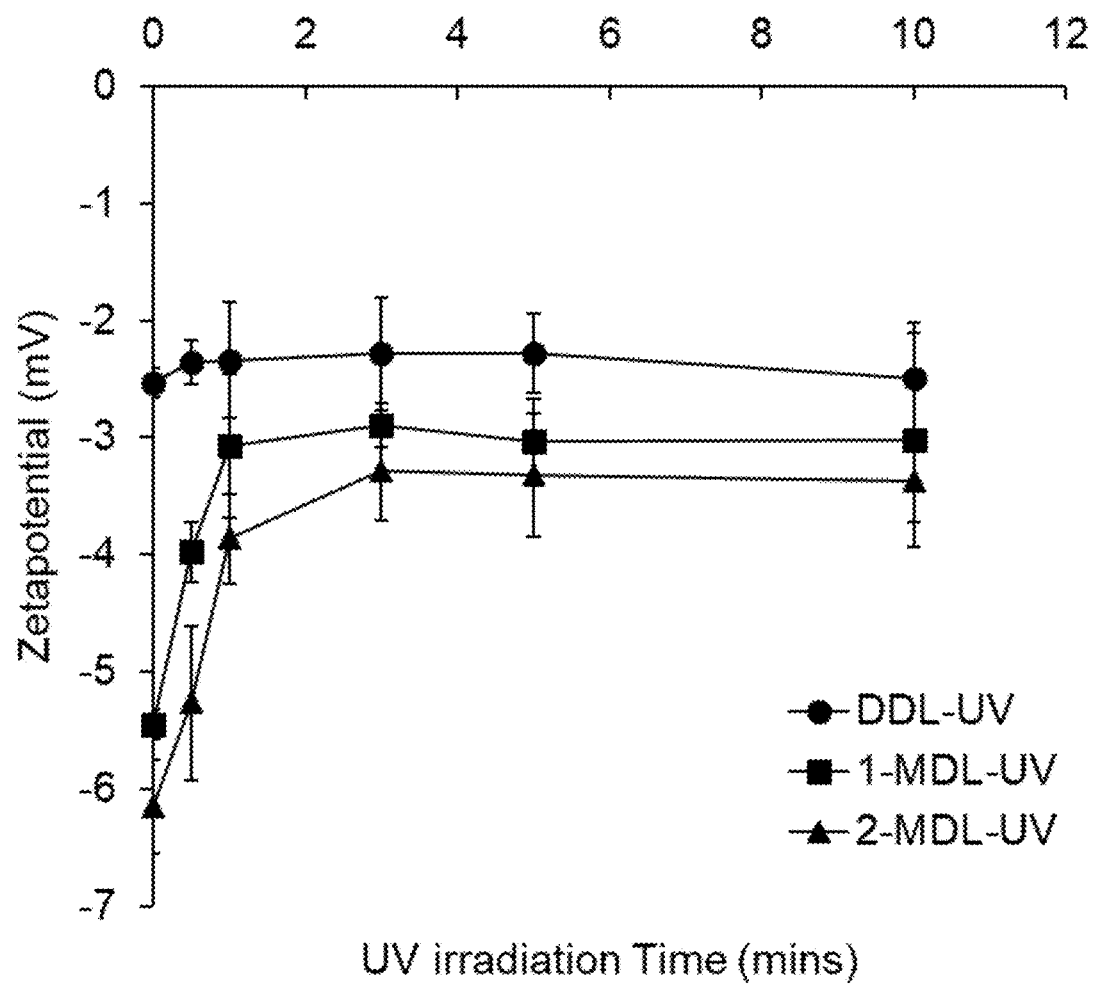
Figure 4C:
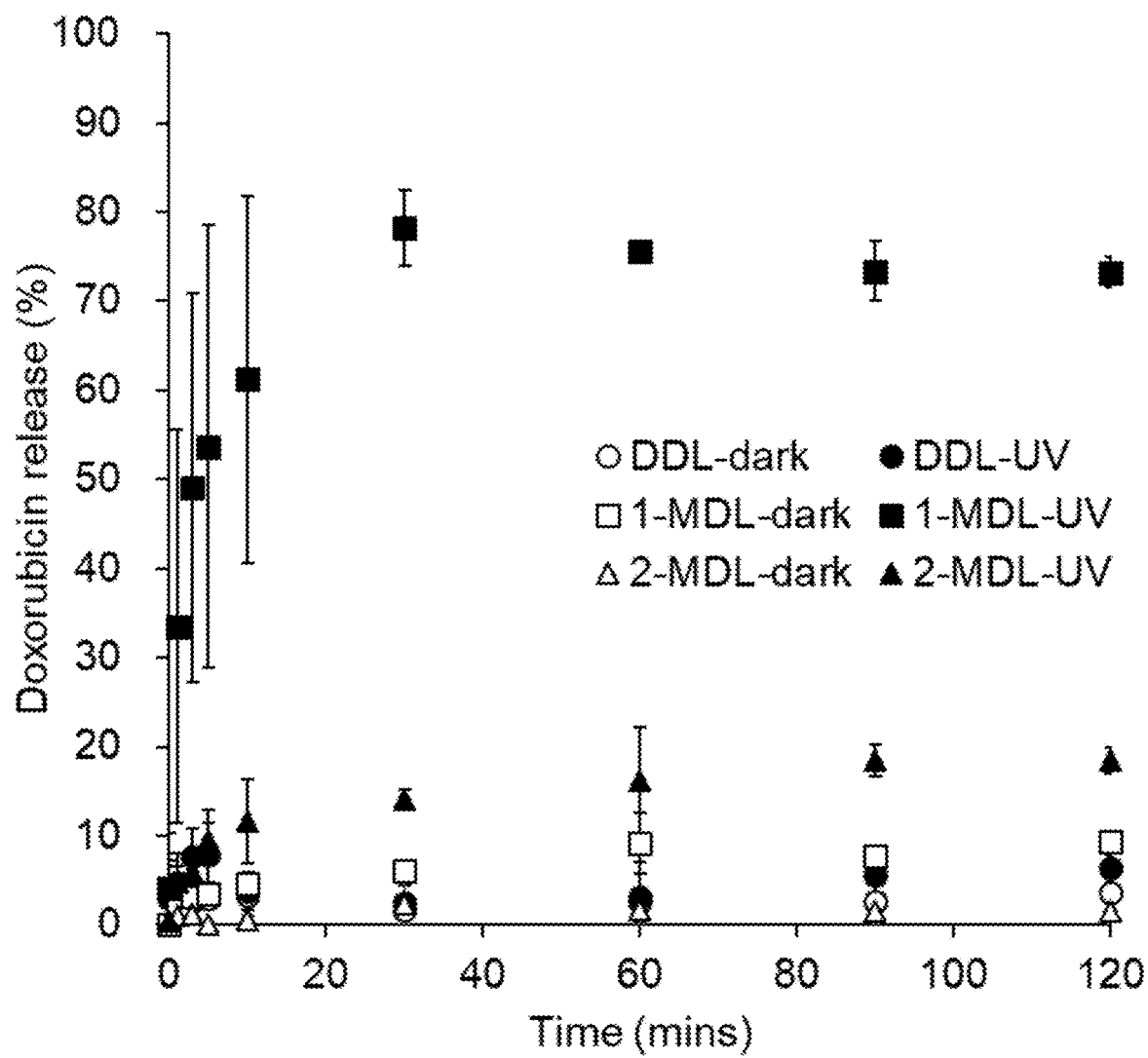

The photolytic removal of poly-glutamate masking motif also can be supported by the time-dependent zeta-potential change upon irradiation, where 1-MDL and 2-MDL displayed a significant increase in zeta-potential while DDL had no change (FIG. 4B). The incubation time needed after irradiation, for DOX to fully escape from liposome, was also screened and release profiles of them were depicted in FIG. 4C. 1-MDL, 2-MDL, and DDL all exhibited no release at dark, no matter how long the incubation time was. However, photo-irradiated 1-MDL exhibited a first order-like fluorescence enhancement (release) curve that required around 30 minutes to complete, while 2-MDL had some basal release, and DDL had almost no release during the 120 minutes incubation period after light irradiation (FIG. 4C). Based on the observation, all the induced liposomal release experiments were subjected to additional 1 hour incubation at 37° C., which is essential for DOX to escape from the liposome.

Figure 4D:
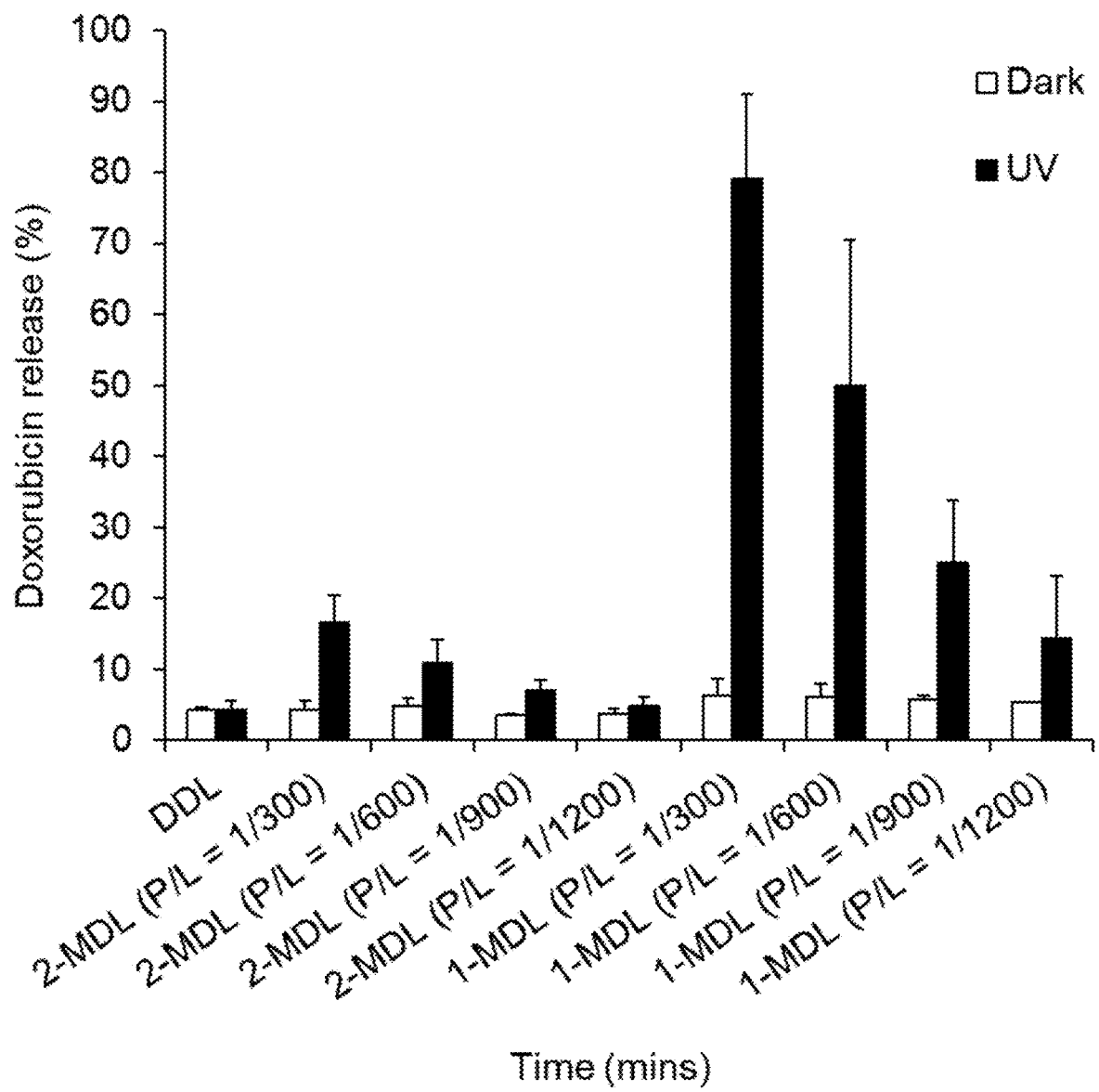

Different peptide/lipid conjugation ratio (ranging from 1/300 to 1/1200) against induced liposomal content release was also screened, and the data was depicted in FIG. 4D. 1-MDL exhibited a greater dynamic range of release (decreasing from 80% to 15%), while the release range of 2-MDL was much less as expected (decreasing from 15% to 3%) after photoirradiation.

Figure 5:
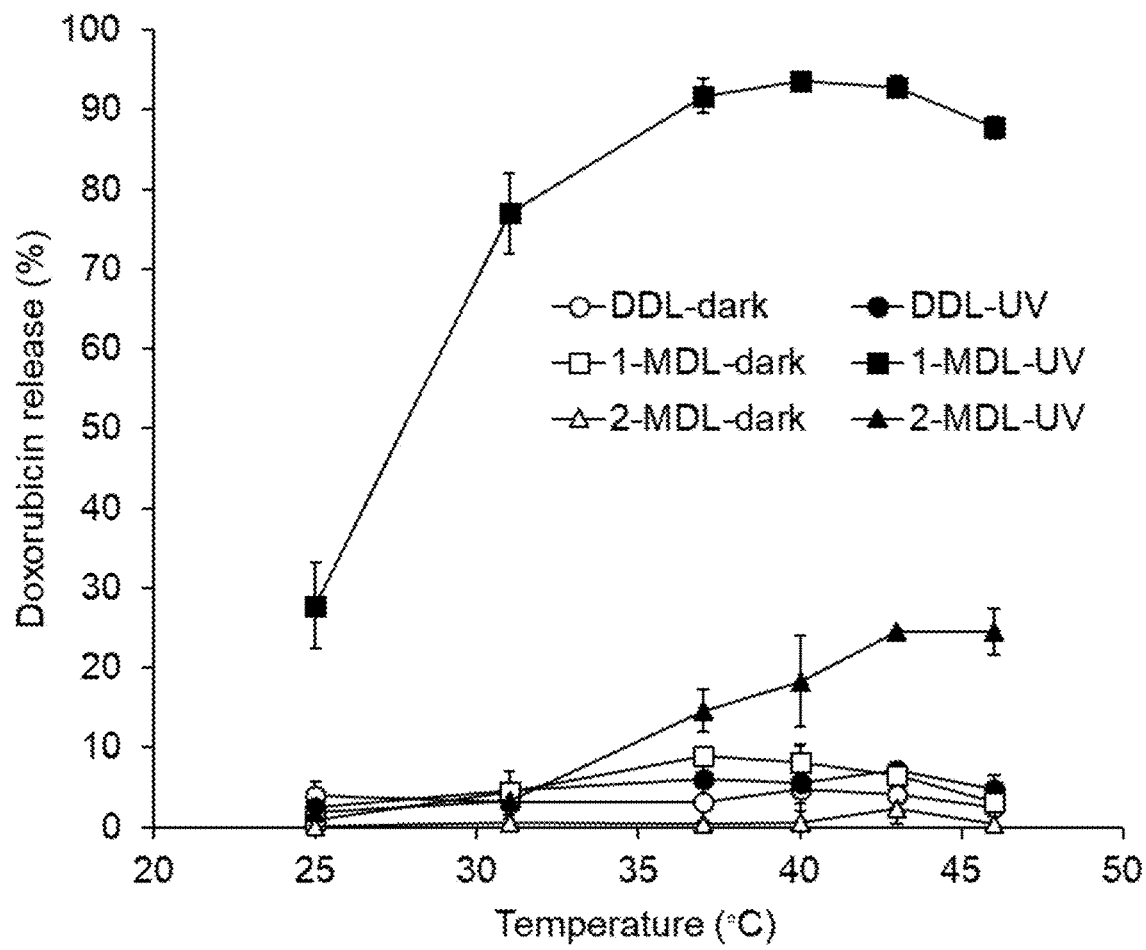
FIG. 5 is a line chart depicting light-induced liposomal release percentages versus incubation temperature according to Example 2.2 of the present disclosure, in which 1-MDL and 2-MDL peptide substitution levels were at peptide/lipid ratio=1/300. The data indicated that at least 37° C. is needed to reach maximal content release.
Figure 6:
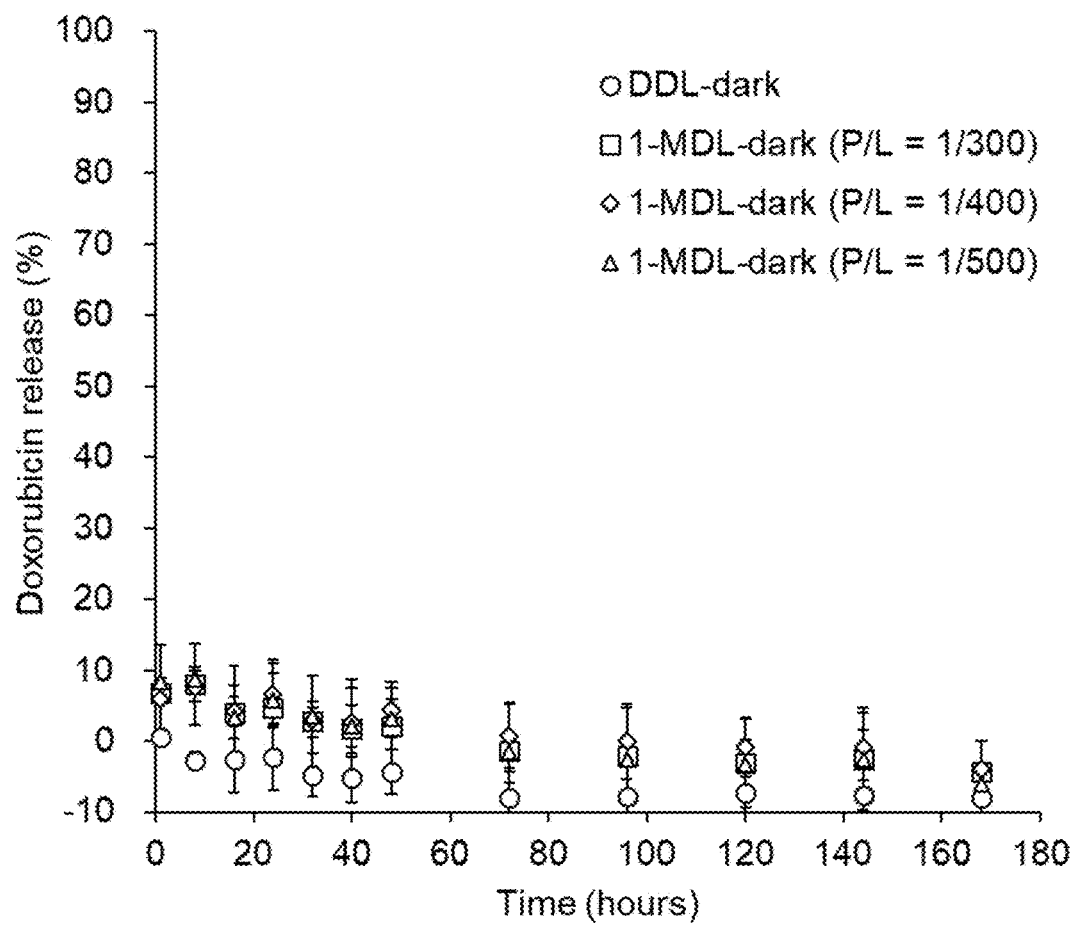
FIG. 6 is a dot plot depicting the long term stability of DDL and 1-MDL with different peptide substitution level (peptide/lipid ratio=1/500, 1/400, and 1/300) in the absence of light at 37° C. according to Example 2.2 of the present disclosure.
Figure 7:
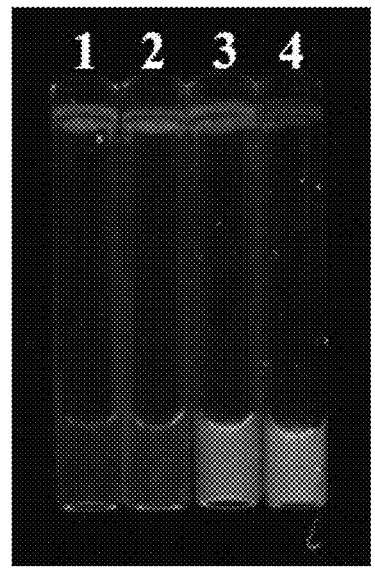
FIG. 7 are images of the liposomal DOX solutions of (1) DDL, (2) 1-MDL, (3) 1-MDL+prior UV irradiation, and (4) 1-MDL+prior Triton™-X100 incubation according to Example 2.2 of the present disclosure. The peptide substitution levels of 1-MDL was at peptide/lipid ratio=1/300. Before (Panel (a)) and after (Panel (b)) UV irradiation, (2) 1-MDL exhibited drastically fluorescence enhancement cause by DOX liposomal escape.
Figure 7:
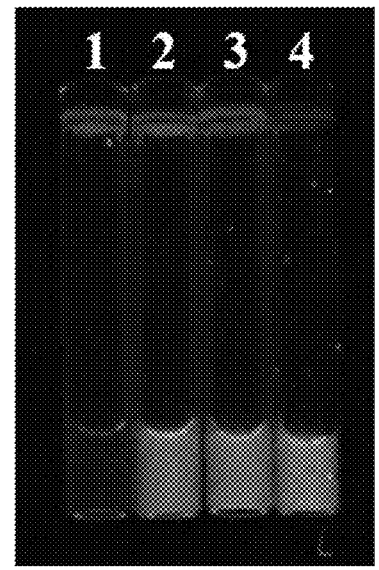

The light-induced content release of peptidyl liposome against temperature, ranging from 25° C. to 46° C., was further screened, and the results were illustrated in FIG. 5. All liposomes incubated without light irradiation showed no significant release even at 46° C., indicating that all the peptidyl and control liposomes are thermally stable before trigger applied. Long term stability of these liposomes was also tested in the absence of light. At a lower temperature such as 25° C., photoactivation of 1-MDL caused a lower release (FIG. 5). Temperature dependency of triggered-release was gradually enhanced when temperature elevated, and saturated at 37° C. (FIG. 5). 2-MDL had the similar temperature dependency but with much lower release dynamic range and the saturation temperature at 43° C. instead of 37° C. after photoactivation (FIG. 5). All liposomes were kept at 37° C. incubator, and did not exhibit any noticeable release for 7-day observation period as depicted in FIG. 6.

To demonstrate the temporal control of light-triggered 1-MDL release, liposomal DOX release was visualized by fluorescence video recording. The video screen snapshot for the liposomal release before (Panel (a)) and after (Panel (b)) light irradiation was depicted in FIG. 7. Test tube #1 contained DDL, where DOX was not released, and therefore, it fluorescently quenched before and after light irradiation. Test tube #2, which contained 1-MDL, exhibited a strong light-induced DOX fluorescence after photoirradiation. Test tubes #3 and #4 displayed pre-photoactivated and detergent-treated full DOX fluorescence of 1-MDL, respectively.

2.3 Drug-Releasing Efficacy Analyzed by Cryo-EM

Figure 8:
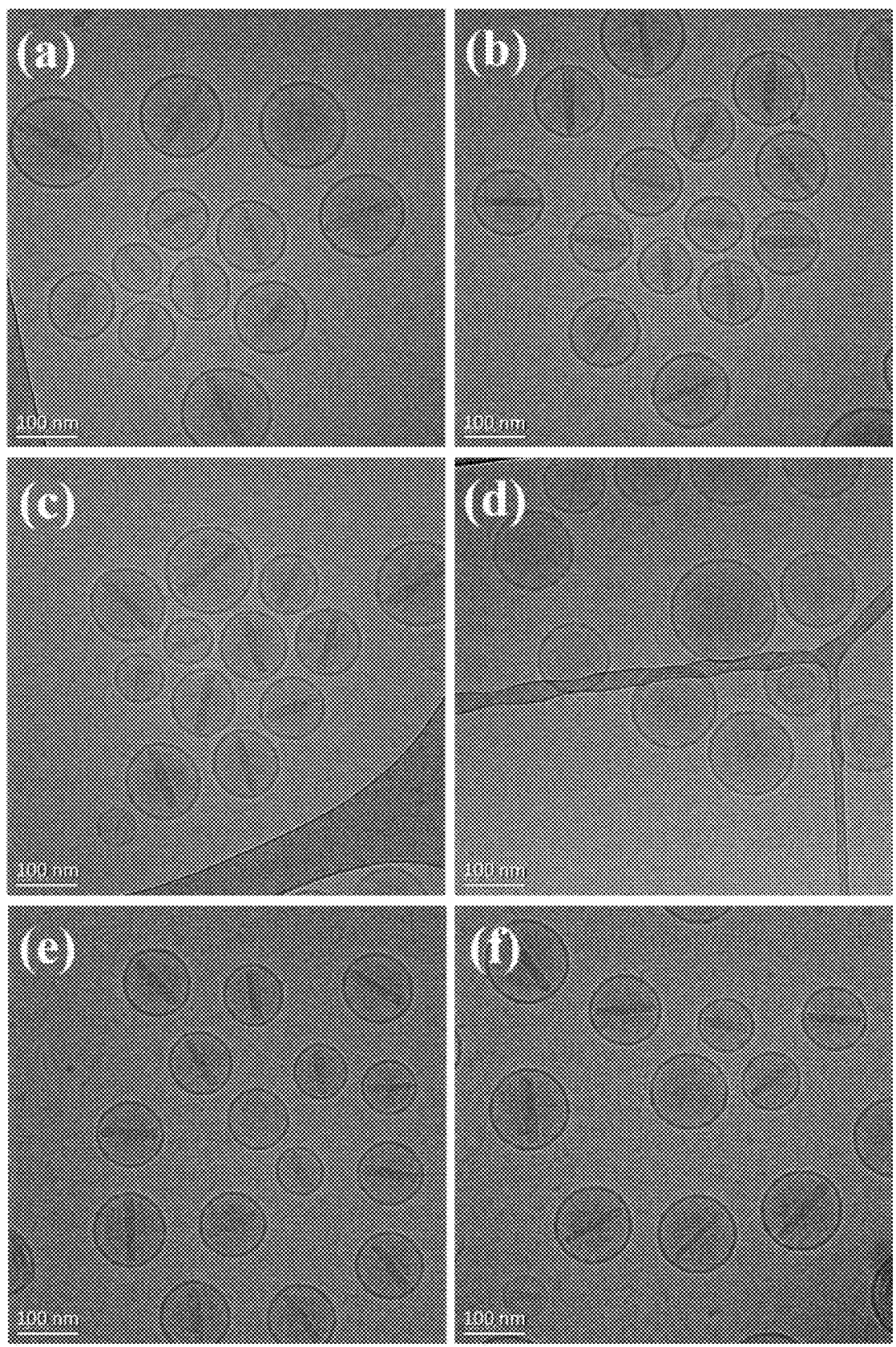
FIG. 8 is the data of cryo-EM according to Example 2.3 of the present disclosure. DOX was stably trapped inside in DDL-dark (Panel (a)), DDL-UV (Panel (b)), 1-MDL-dark (Panel (c)), 2-MDL-dark (Panel (e)), and 2-MDL-UV (Panel (f)). The peptide substitution levels of 1-MDL and 2-MDL were at peptide/lipid ratio=1/300. DOX significantly escaped only from 1-MDL-UV (Panel (d)). Both 2-MDL-dark (Panel (e)), and 2-MDL-UV (Panel (f)) had DOX trapped inside liposome. Scale bar: 100 nm in all images.

The morphology of all liposomes was further examined by cryo-EM. Before triggering signal, DOX-loaded liposomes were all well-dispersed, uniform in size, and slightly oval-shaped with approximately 130 nm in diameter, like commercial DOX liposome or the control liposome, where both have no peptide conjugated on surface (FIG. 8, Panels (a) and (b)). Before photoactivation of 1-MDL and 2-MDL, there was no change in morphology (FIG. 8, Panels (c) and (e)). However, after photoactivation of 1-MDL, the encapsulated DOX released and more hollowed liposomes were generated as shown in FIG. 8, Panel (d). On the contrary, the encapsulated DOX still remained trapped inside 2-MDL after light irradiation (FIG. 8, Panel (f)). Because statistically significant amount of liposomal cryo-EM images was acquired (>$10^3$ liposomes), the light-induced liposomal release percentages were quantified directly based on the cryo-EM images, in which 1-MDL-dark possessed a release of 3%, while 1-MDL-UV exhibited a 73% release (data not shown). 2-MDL-dark and 2-MDL-UV both possessed a very low release, 3% and 12%, respectively (data not shown).

These results demonstrate that DOX release percentage estimated by fluorescence dequenching assay, match well with the release percentage calculated from the individual liposome counts in cryo-EM images, based on the observation that the liposomal release belongs to all-or-nothing released type.

2.4 Cellular Uptake of Peptidyl Liposomal DOX and Trigger-Release DOX

The intracellular localization of DOX reveals the importance of trigger-release liposome. Fluorescence images of KB cells treated with free DOX, DDL, and 1-MDL in the presence and absence of light irradiation were recorded. DOX is anthracycline drug, which is membrane permeable, has a high affinity with DNA, and can interfere topoisomerase II activity. Hence, free DOX can be retained and concentrated in the cell nucleus, while liposomal DOX will remain in cytosol or endosome/lysosome. Cells treated with DDL-dark, 2-MDL-dark, and 1-MDL-dark showed a punctate DOX fluorescence in the cytosol but in the cell nucleus, suggesting that DOX remained stably trapped inside liposome (while liposome is trapped inside endosome), and the insufficient DOX uptake was probably due to the limited endocytosis turnover cycles (data not shown). Liposome has no trigger release function, hence requires much higher dose and longer liposomal degradation time to generate the same extent of DOX uptake, as Free DOX (data not shown). In contrast, although KB cells incubated with 1-MDL-dark exhibited a similar fluorescence pattern as DDL-dark, KB cells incubated with 1-MDL-UV exhibited a significant DOX uptake, and displayed an intense DOX fluorescence in cytosol and nucleus (data not shown). 1-MDL-UV quantitatively released the DOX content, diffused into KB cell and maximized DOX uptake (data not shown). Free DOX treated KB cells showed the maximal uptake of 12.5 μM DOX (data not shown). 1-MDL-UV, compared with free DOX, released similar amount of DOX for cells to uptake, but provided an additional trigger design to switch-on the release.

Consistent with these findings, cellular DOX amount and the consequent apoptosis were quantitatively evaluated. For these studies, KB cells treated with DDL, 1-MDL and free DOX in the presence and absence of light irradiation were analyzed using flow cytometry and high content confocal quantitative image cytometer (data not shown) where cellular DOX fluorescence intensity (DOX uptake) was plotted against Annexin-V fluorescence intensity (extent of apoptosis). DDL and 1-MDL-dark treated KB cells exhibited a minimal DOX uptake with a minimal apoptosis extent. On the other hand, 1-MDL-UV quantitatively released the large amount of DOX, maximized cellular DOX uptake, and consequently caused a high percentage of apoptosis (data not shown). The same trend is observed for KB cells treated with free DOX (data not shown).

2.5 Dose-Dependent Cellular Toxicity of Photoactivated Liposomes

Figure 9:
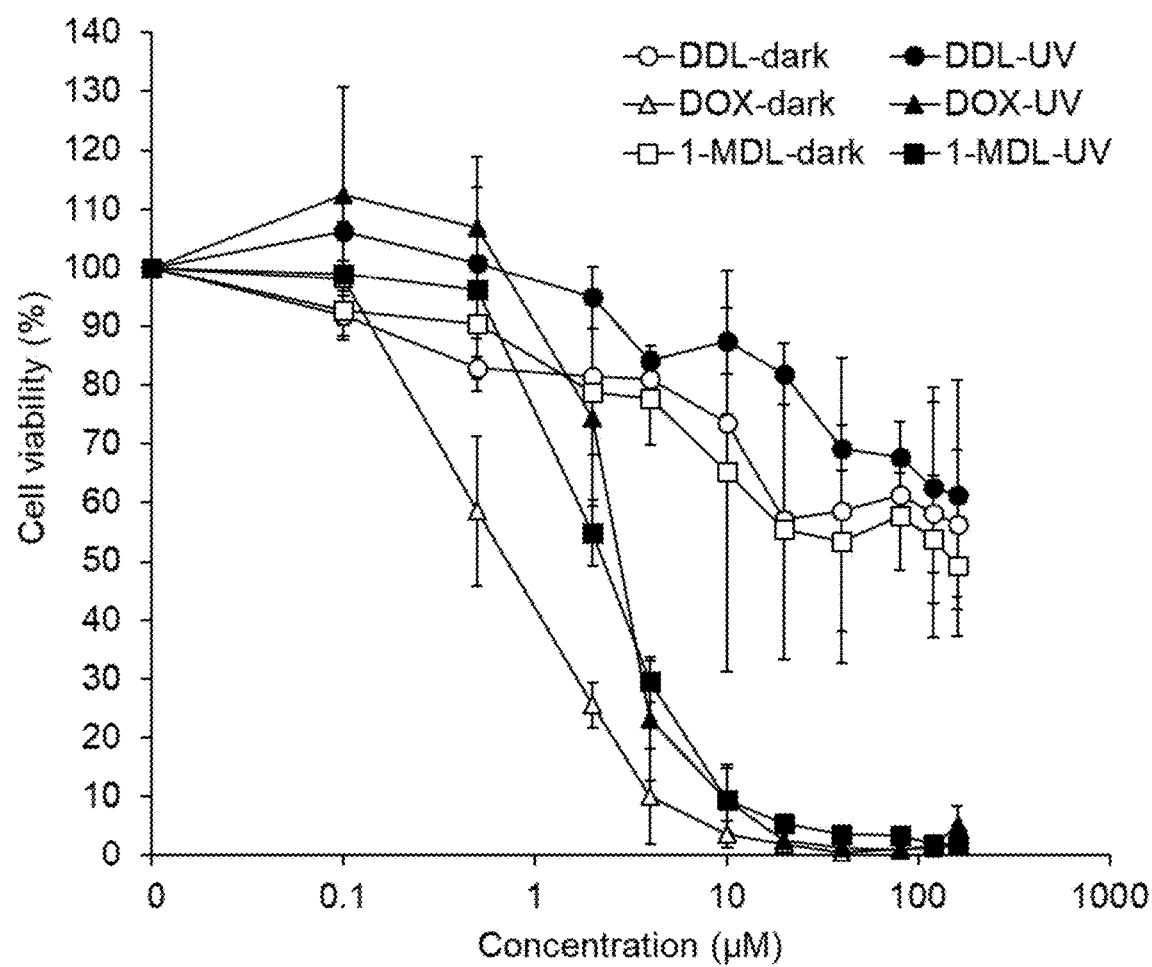
FIG. 9 is a line chart depicting cell viability of KB cells according to Example 2.5 of the present disclosure. Cells treated with liposomal DOX, and free DOX were either irradiated (4 minutes) or non-irradiated before 40 hours incubation. The peptide substitution level of 1-MDL was at peptide/lipid ratio=1/300. DDL-dark, DDL-UV, and 1-MDL-dark exhibited $IC_{50}$>160 µM, while 1-MDL-UV exhibited $IC_{50}$ about 2 µM similar to DOX-dark ($IC_{50}$ about 0.7 µM) and DOX-UV ($IC_{50}$ about 3 µM). Photoactivation made the DOX efficacy of 1-MDL 80 folds higher.

The dose-dependent cytotoxicity of free DOX, DDL and 1-MDL in the presence or absence of UV irradiation towards KB cells was evaluated using MTT assay with DOX apparent concentration ranging from 0.1 to 160 μM. According to the data of FIG. 9, the cytotoxicity of 1-MDL-UV, in terms of $IC_{50}$, was about 2 μM which was similar to DOX-dark (0.7 μM) and DOX-UV (3 μM), while the liposomes without trigger-release (DDL-dark, DDL-UV, and 1-MDL-dark) all needed a very high apparent concentration of DOX to be equally effective ($IC_{50}$>160 μM). Before light irradiation, 1-MDL exhibited a low toxicity (high $IC_{50}$ value) similar to conventional DOX liposomes but provided an 80-fold enhancement of the induced cytotoxicity after triggering (FIG. 9). The provided dynamic range of toxicity has the potential to be turned on at the intended site of action. These data reveal that the dose of traditional liposome, once equip with trigger-release mechanism, can widen its therapeutic window.

Example 3 Characterization of Liposomes 3-MDL and 4-MDL

Figure 10A:
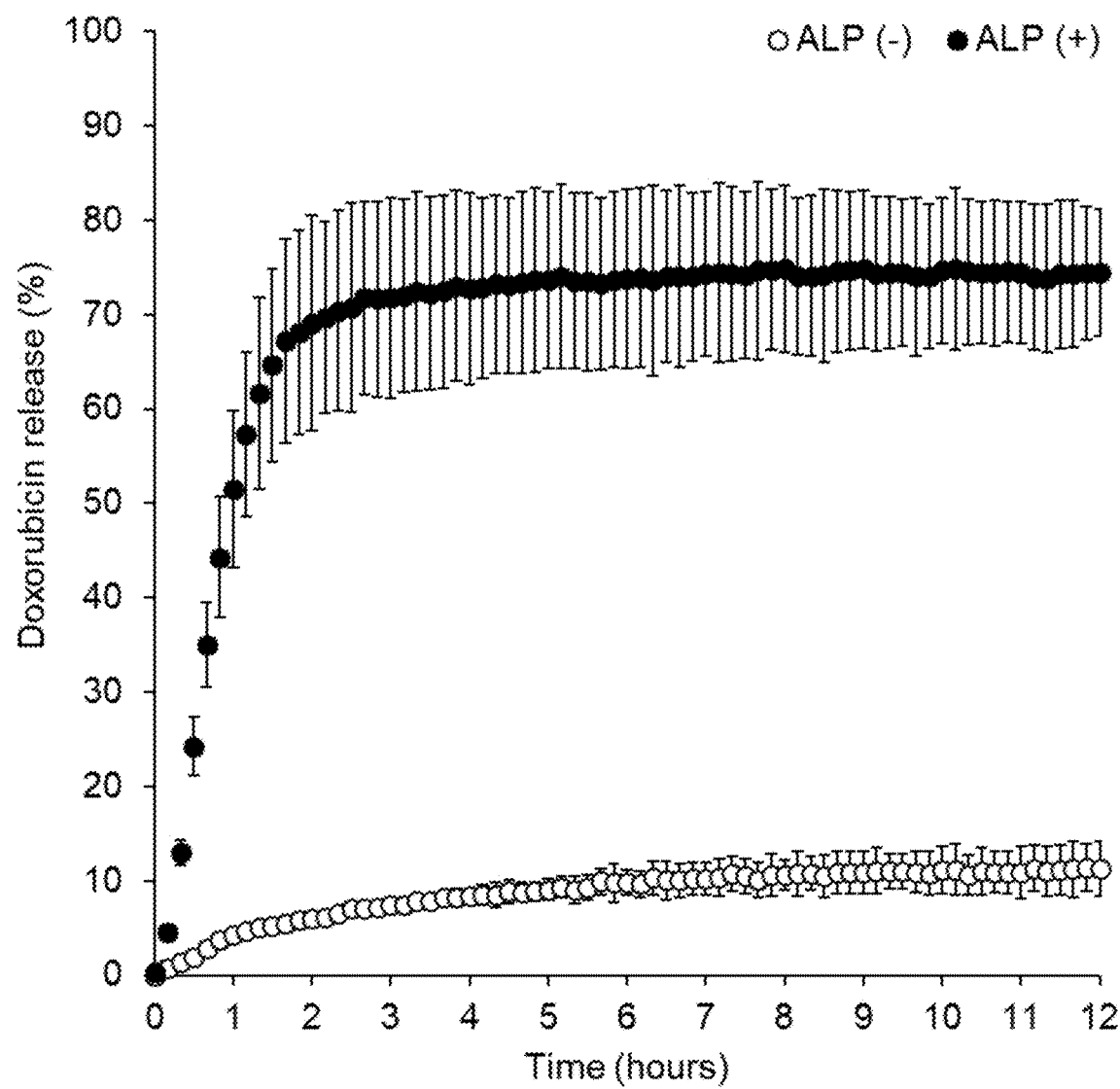
FIGS. 10A and 10B are drug-releasing results of liposomes 3-MDL (FIG. 10A) and 4-MDL (FIG. 10B) with or without ALP treatment according to Example 3 of the present disclosure. ALP: alkaline phosphatase.

According to the DOX release kinetics of 3-MDL containing 0%, 1.66%, 3.33% or 5% PEF2000 lipid, 5% PEGylated 3-MDL was observed that 3 hours of ALP incubation was sufficient to maximize the release for 3-MDL (FIG. 10A). Fluorescence images of HS-5 and KB cells treated with free DOX, DDL, and 3-MDL with high and low ALP expression are recorded, in which all the liposomes and free DOX had apparent DOX concentrations at 12.5 μM, while the 3-MDL exhibited significant release in KB cells (which has high ALP expression) as compared to HS-5 cells (which has low ALP expression) (data not shown).

Figure 10B:
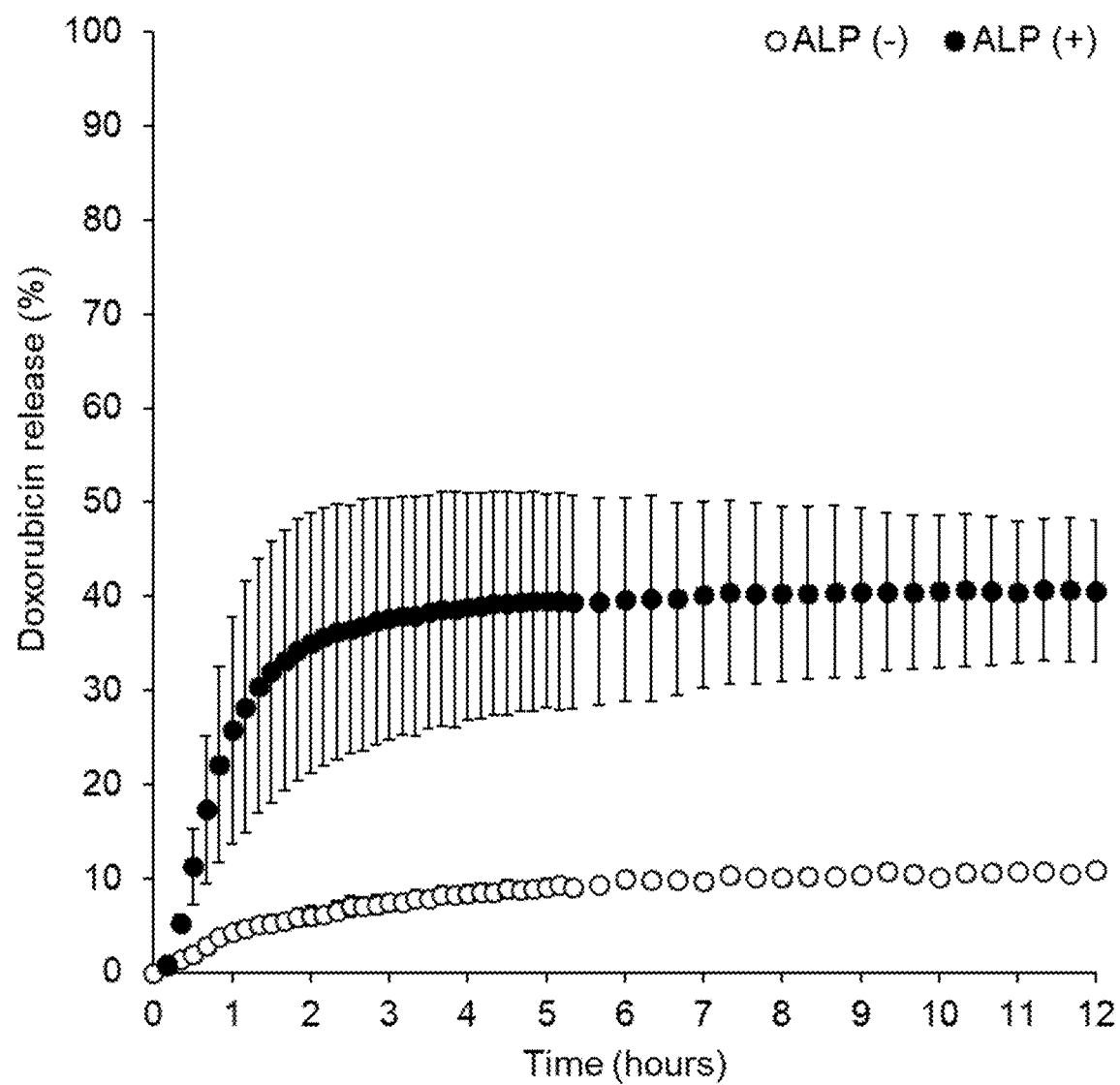

PEG2000 lipid percentage for optimal 4-MDL liposomal (peptide/lipid ratio=1/300) release with ALP enzymes was also screened (data not shown). The data indicated that 2% PEGylated 4-MDL had the optimal DOX release percentage (FIG. 10B). 2% PEGylated 4-MDL although exhibited slightly higher release, however, the basal release was also higher. The trigger-release extent of 5% PEGylated 4-MDL was unsatisfactory due to PEG2000 lipid would hinder the ALP. The less release of the 4-MDL was probably due to the incomplete dephosphorylation.

Example 4 Characterization of Liposomes 5-MDL and 6-MDL

REF52 cells (low MMP2 expression) were incubated with free DOX, or liposomes in medium containing (1) no MMP2, (2) commercial active MMP2 (300 ng/ml), or (3) HT1080 conditioned medium at 37° C. for 20 hours. All the liposomes, including DDL and 5-MDL, and free DOX had apparent DOX concentrations at 12.5 μM (data not shown). Cells incubated with the 5-MDL (with or without PEG2000 lipid) in active MMP2 or HT1080 conditioned medium all exhibited DOX release, while REF52 cells incubated with DDL (with or without PEG2000 lipid) with active MMP2 or HT1080 conditioned medium, exhibited no DOX release (data not shown).

The unsatisfactory release of the 6-MDL was probably due to the adverse uncaging kinetics of peptide 6 (data not shown).

Example 5 Characterized of Liposomes Containing Cy5.5, or $Gd^{3+}$-DTPA

In addition to DOX, other agents, including Cy5.5, and $Gd^{3+}$-DTPA, were also respectively loaded to the liposomes with peptide 1 coupled on the lipid. The analytic results were described in this example.

Figure 11:
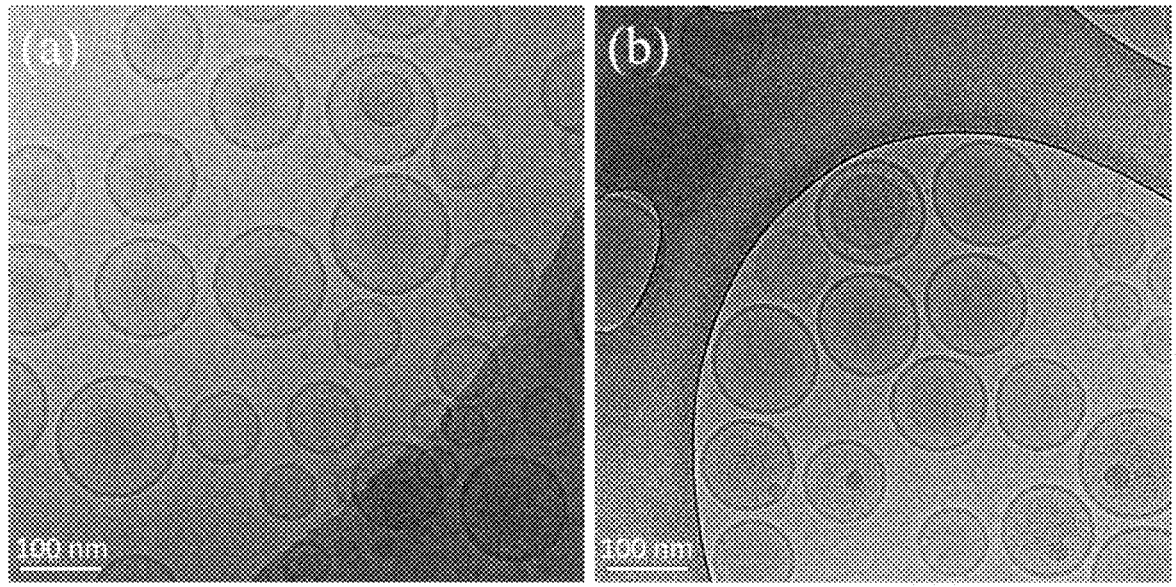
FIG. 11 are cryo-EM images of empty liposomes (Panel (a)) and Cy5.5 encapsulated liposomes (Panel (b)) according to Example 5 of the present disclosure. Scale bar: 100 nm in all images.

According to the data of cryo-EM, Cy5.5 was successfully encapsulated in the liposomes using calcium acetate and sucrose octasulfate ammonium as trapping agents, respectively (FIG. 11).

Further, $Gd^{3+}$-DTPA was passive-loaded into liposomes by hydrating the lipid film using 200 mM $Gd^{3+}$-DTPA. The detailed sizes and zeta-potentials of $Gd^{3+}$-DTPA liposomes are listed in Table 5.

TABLE 5

Hydrodynamic diameter and zeta-potential characterization of specified liposomes in the presence or absence of light irradiation

| Samples | Diameter (nm) | PDI | Zeta-potential (mV) |
| --- | --- | --- | --- |
| GL-dark | 128 ± 33 | 0.04 ± 0.01 | −2.1 ± 0.2 |
| DGL-dark | 129 ± 33 | 0.05 ± 0.00 | −2.4 ± 0.7 |
| DGL-UV | 128 ± 32 | 0.04 ± 0.01 | −1.7 ± 0.3 |
| 1-MGL-dark | 129 ± 34 | 0.06 ± 0.02 | −2.3 ± 0.6 |
| 1-MGL-UV | 130 ± 33 | 0.05 ± 0.02 | −1.8 ± 0.6 |

GL: $Gd^{3+}$-DTPA liposome; DGL: DTT conjugated $Gd^{3+}$-DTPA liposome; 1-MGL: peptide 1 conjugated $Gd^{3+}$-DTPA liposome.

Figure 12A:
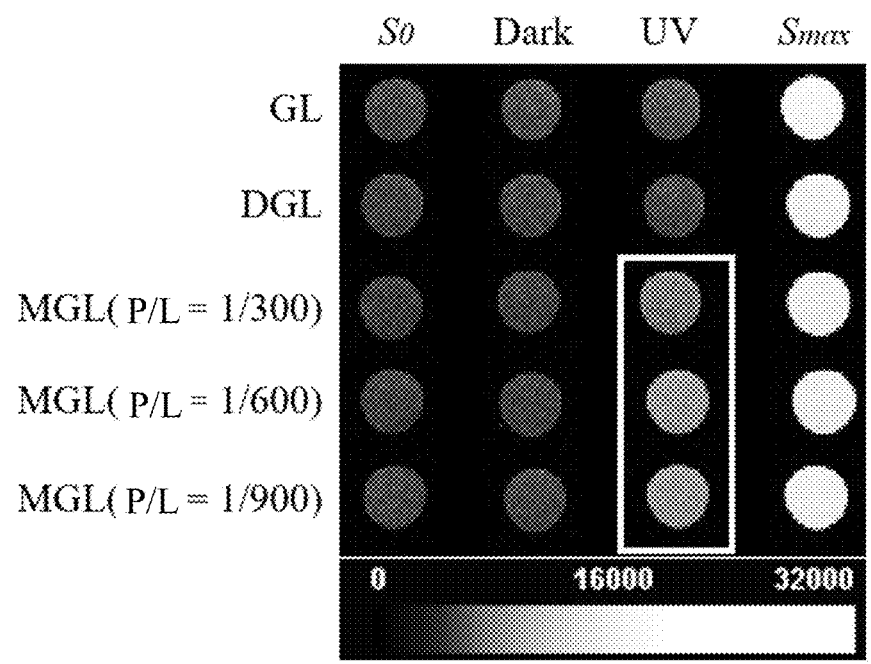
FIGS. 12A and 12B are photograms of photo-induced 1-MGL liposomal release with different peptide substitution levels at peptide/lipid ratio=1/900, 1/600, and 1/300.
Figure 12B:
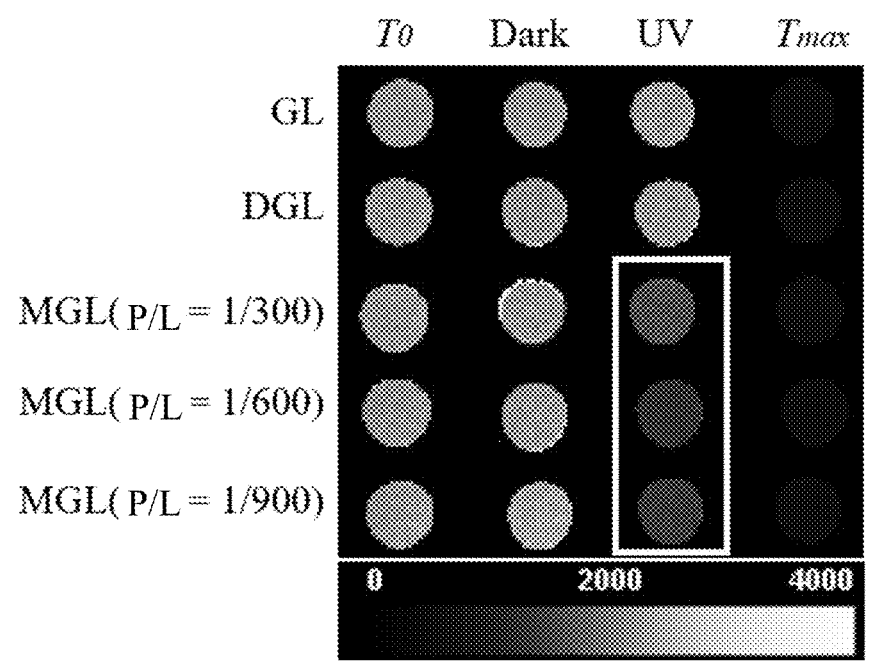

The data of FIGS. 12A and 12B indicated that 1-MGL exhibited a strong Gd'-DTPA contrast enhancement upon light-induced release in both $T_1$-weighted relaxation rate (FIG. 12A) and $T_1$-map signals (FIG. 12B) as compared to DGL.

In conclusion, the present disclosure provides several types of liposomes respectively having specified polypeptides coupled thereto. Once being activated by a proper stimulation (for example, light or enzyme), the present liposomes are capable of releasing the encapsulated agent or molecule in target sites. Accordingly, the present liposome provides a potential means to diagnose or treating diseases in a safer and more accurate manner.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A liposome comprising, a center core, a lipid layer encapsulating the center core, and a synthetic polypeptide coupled to the lipid layer, wherein the synthetic polypeptide consists of a membrane lytic motif, a masking motif, and a linker configured to link the membrane lytic motif and the masking motif, wherein the membrane lytic motif is a peptide consisting of SEQ ID NO: 3;

the masking motif is a peptide consisting of 12 negative-charged amino acid residues; and the linker is a photocleavable or protease-cleavable moiety, wherein the photocleavable moiety is of the structure of formula (I) or formula (II):

(I)

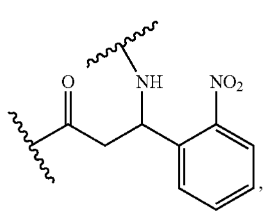

-continued (II)

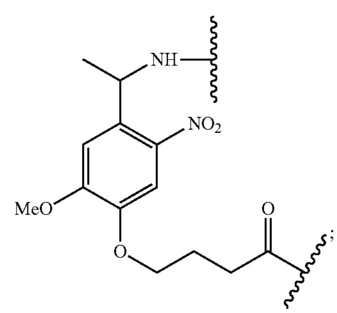

and the protease-cleavable moiety consists of the amino acid sequence of SEQ ID NO: 23 or 24.

2. The liposome of claim 1, wherein the center core comprises a therapeutic agent or a reporter molecule.

3. The liposome of claim 2, wherein the therapeutic agent is selected from the group consisting of an anti-tumor agent, an anti-inflammatory agent, an anti-microbial agent, an anti-oxidant agent, a growth factor, a neuron transmitter, and a protein inhibitor.

4. The liposome of claim 3, wherein the therapeutic agent is the anti-tumor agent or the protein inhibitor.

5. The liposome of claim 2, wherein the reporter molecule is a contrast agent, or a fluorescent molecule.

6. A method of diagnosing or treating a disease in a subject, comprising administering to the subject an effective amount of the liposome of claim 1.

7. The method of claim 6, wherein the subject is a human.

* * * * *